(12) United States Patent
Patil et al.

(10) Patent No.: US 12,714,376 B2
(45) Date of Patent: Aug. 25, 2026

(54) MULTI-LAYERED ARTICULATING PATIENT SUPPORT FOR A MEDICAL IMAGING SYSTEM AND A CONTROL SYSTEM THEREOF

(71) Applicant: GE Precision Healthcare LLC, Waukesha, WI (US)

(72) Inventors: Mahendra Madhukar Patil, Bangalore (IN); Nicole Louisa de Klein, Amsterdam (NL); Sachin Arya, Sonipat (IN)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/927,155

(22) Filed: Oct. 25, 2024

(65) Prior Publication Data

US 2026/0114825 A1 Apr. 30, 2026

(51) Int. Cl.

*A61B 6/04* (2006.01)
*A61B 6/03* (2006.01)
*A61B 6/10* (2006.01)

(52) U.S. Cl.

CPC ............ *A61B 6/0407* (2013.01); *A61B 6/032* (2013.01); *A61B 6/0478* (2013.01); *A61B 6/102* (2013.01)

(58) Field of Classification Search

CPC .. A61H 2003/046; A61H 3/04; A47C 17/162; A61G 7/16; A61G 7/015; A61G 2200/34; A61G 7/0507; A61G 7/0514; A61G 7/053; A61G 5/006; A61G 7/005; A61G 13/0018; A61G 13/02; A61G 13/06; A61G 13/08; A61G 13/1225; A61G 13/1245; A61G 13/125; A61G 15/02;
(Continued)

(56) References Cited

U.S. PATENT DOCUMENTS 6,295,671 B1 10/2001 Reesby et al.
6,336,235 B1 1/2002 Ruehl
(Continued)

FOREIGN PATENT DOCUMENTS

CN 107348741 11/2017

OTHER PUBLICATIONS

PCT Application No. PCT/US2025/050718, International Search Report and Written Opinion, mailed Jan. 20, 2026, 13 pgs.

*Primary Examiner* — Mark D Remaly
(74) *Attorney, Agent, or Firm* — Fletcher Yoder, P.C.

(57) ABSTRACT

A patient table for a medical imaging system includes a multi-layered patient support including a top patient support configured to articulate and a bottom patient support, wherein the multi-layered patient support is configured to support a subject to be imaged, and wherein the top patient support is configured to move between a first configuration where the top patient support is flat and horizontal to support the subject in a recumbent position and a second configuration where the top patient support is in an upright-chair configuration to support the subject in an upright seated position. The patient table also includes a platform, wherein the platform is coupled to and supports the multi-layered patient support, and wherein the platform is configured to keep the multi-layered patient support at a desired elevation and to move the multi-layered patient support into and out of a bore of a gantry of the medical imaging system.

20 Claims, 15 Drawing Sheets

(58) Field of Classification Search
CPC ...... A61G 15/12; A61G 2200/32; A61G 5/14; A61G 7/00; A61G 7/012; A61G 7/018; A61G 7/0506; A61G 7/052; A61G 7/1076; A61G 2200/36; A61G 2203/20; A61G 2203/74; A61G 7/002; A61G 7/008; A61G 7/0509; A61G 7/0513; A61G 7/0524; A61G 7/0527; A61G 7/1021
See application file for complete search history.

(56) References Cited

U.S. PATENT DOCUMENTS

| | | | | |
|---|---|---|---|---|
| 6,441,576 | B1 | 8/2002 | Marin-Martinod et al. | |
| 6,752,463 | B2 | 6/2004 | Nivet | |
| 7,911,163 | B2 | 3/2011 | Nivet | |
| 8,127,380 | B2 | 3/2012 | Wurdeman | |
| 8,640,285 | B2 | 2/2014 | Heimbrock et al. | |
| 9,265,677 | B2 | 2/2016 | Manouchehri et al. | |
| 10,188,567 | B2 | 1/2019 | Wurdeman | |
| 10,632,037 | B2 | 4/2020 | Baker et al. | |
| 10,898,402 | B2 | 1/2021 | Baker et al. | |
| 11,052,005 | B2 | 7/2021 | Childs et al. | |
| 11,458,056 | B2 | 10/2022 | Poulos et al. | |
| 2010/0172468 | A1* | 7/2010 | Gregerson | A61B 6/0407 378/208 |
| 2012/0324648 | A1 | 12/2012 | Amano | |
| 2016/0151025 | A1 | 6/2016 | Gatayama et al. | |
| 2022/0117816 | A1* | 4/2022 | Furman | A61G 7/018 |

* cited by examiner 64
122
138

64
222
46
62
162
220
222
220

MULTI-LAYERED ARTICULATING PATIENT SUPPORT FOR A MEDICAL IMAGING SYSTEM AND A CONTROL SYSTEM THEREOF

BACKGROUND

The subject matter disclosed herein relates to imaging systems and, more particularly, to multi-layered articulating patient support for a medical imaging system.

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray based imaging technologies, X-ray radiation spans and is transmitted through a subject of interest, such as a human patient, and a portion of the X-ray radiation impacts an X-ray detector where image data is collected. In digital X-ray systems a photodetector produces signals representative of the amount or intensity of X-ray radiation impacting discrete pixel regions of X-ray detector elements or sensors. The signals may then be processed to generate an image that may be displayed for review.

Safely handling and positioning patients during imaging procedures is a strenuous and time-consuming task especially for geriatric, frail, physically impaired, or injured patients. Often additional support staff is required to physically assist the patients while positioning them suitably for an imaging procedure.

SUMMARY

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, a patient table for a medical imaging system is provided. The patient table includes a multi-layered patient support including a top patient support configured to articulate and a bottom patient support, wherein the multi-layered patient support is configured to support a subject to be imaged, and wherein the top patient support is configured to move between a first configuration where the top patient support is flat and horizontal to support the subject in a recumbent position and a second configuration where the top patient support is in an upright-chair configuration to support the subject in an upright seated position. The patient table also includes a platform, wherein the platform is coupled to and supports the multi-layered patient support, and wherein the platform is configured to keep the multi-layered patient support at a desired elevation and to move the multi-layered patient support into and out of a bore of a gantry of the medical imaging system for an imaging procedure performed on the subject.

In another embodiment, a medical imaging system is provided. The medical system includes a gantry having a bore and coupled to imaging components configured to acquire imaging data of a subject. The medical imaging system also includes a patient table integrated with the gantry. The patient table includes a multi-layered patient support including a top patient support configured to articulate and a bottom patient support, wherein the multi-layered patient support is configured to support the subject to be imaged, and wherein the top patient support is configured to move between a first configuration where the top patient support is flat and horizontal to support the subject in a recumbent position and a second configuration where the top patient support is in an upright-chair configuration to support the subject in an upright seated position. The patient table also includes a platform, wherein the platform is coupled to and supports the multi-layered patient support, and wherein the platform is configured to move the multi-layered patient support into and out of the bore of the gantry of the medical imaging system for an imaging procedure performed on the subject.

In a further embodiment, a medical imaging system is provided. The medical system includes a gantry having a bore and coupled to imaging components configured to acquire imaging data of a subject. The medical imaging system also includes a patient table integrated with the gantry. The patient table includes a multi-layered patient support including a top patient support configured to articulate and a bottom patient support, wherein the multi-layered patient support is configured to support the subject to be imaged, and wherein the top patient support is configured to move between a first configuration where the top patient support is flat and horizontal to support the subject in a recumbent position and a second configuration where the top patient support is in an upright-chair configuration to support the subject in an upright seated position. The patient table also includes a platform, wherein the platform is coupled to and supports the multi-layered patient support, and wherein the platform is configured to move the multi-layered patient support into and out of the bore of the gantry of the medical imaging system for an imaging procedure performed on the subject. The patient table further includes a plurality of sensors coupled to the multi-layered patient support. The patient table still further includes a plurality of actuators coupled to multi-layered patient support. The patient table even further includes a controller including a memory and a processing system including one or more processors, wherein the controller is configured to receive feedback from the plurality of sensors, to estimate both a subject's pose and exerted physical effort towards either ingress into or egress from the top patient support based on the feedback, to calculate respective assistive forces needed at various portions of the top patient support based on the subject's pose and exerted physical effort, and to provide control signals to the plurality of actuators to deliver the respective assistive forces at the various portions of the top patient support.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

Figure 1:
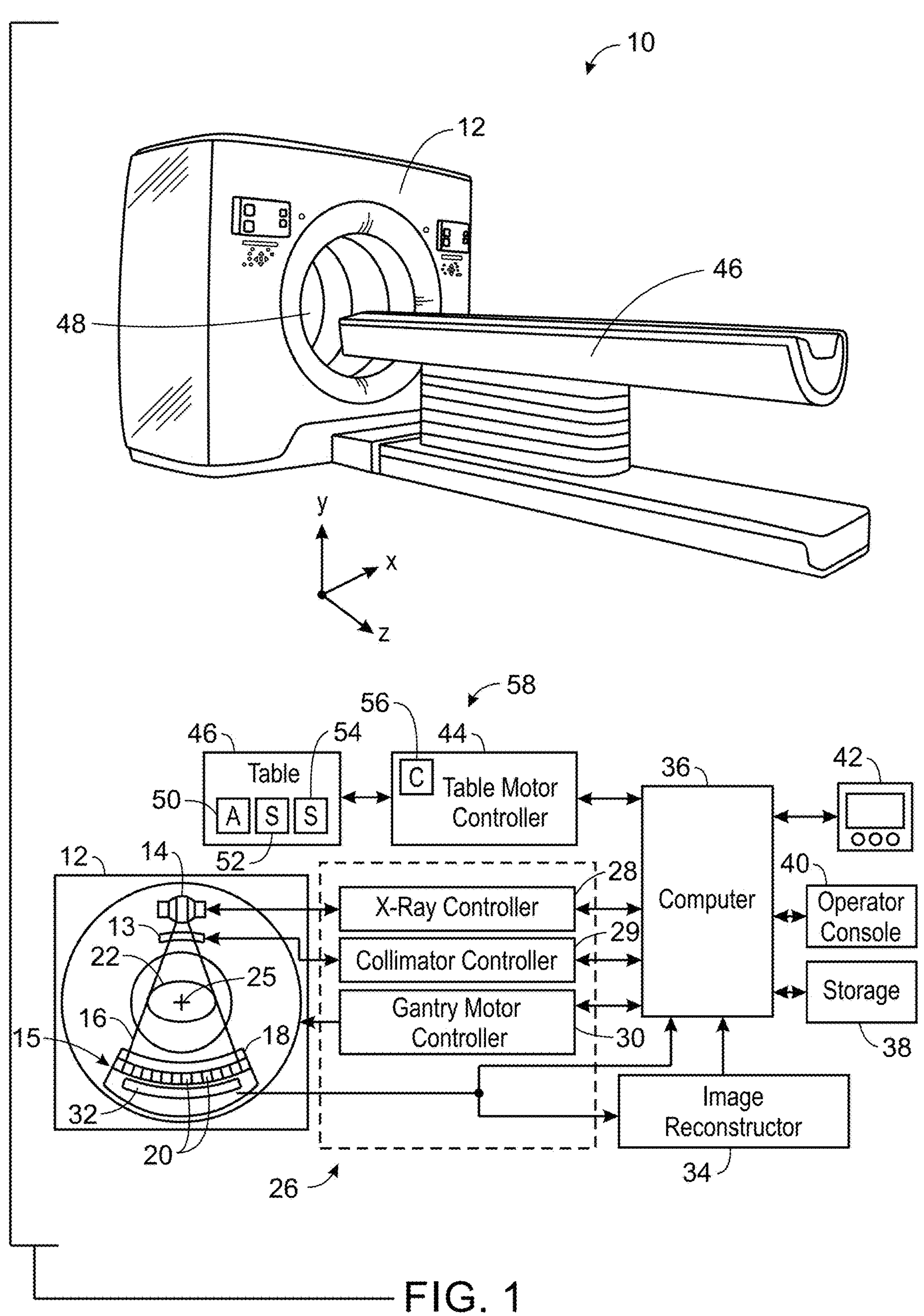
FIG. 1 is a combined pictorial view and block diagram of a computed tomography (CT) imaging system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts, such as image reconstruction for non-destructive inspection of manufactured parts or goods (i.e., quality control or quality review applications), and/or the non-invasive inspection of packages, boxes, luggage, and so forth (i.e., security or screening applications). In general, the disclosed techniques may be useful in any imaging or screening context or image processing or photography field where a set or type of acquired data undergoes a reconstruction process to generate an image or volume.

The present disclosure provides embodiments for a patient table of medical imaging systems (e.g., a computed tomography (CT) imaging system, magnetic resonance imaging (MRI) system, positron emission tomography (PET) imaging system, single-photon emission computed tomography (SPECT) imaging system, nuclear medicine imaging system, X-ray imaging system, or any combinations thereof etc.). The patient table may be integrated with a gantry of the medical imaging system. The patient table includes a multi-layered articulating patient support. The patient table also includes intelligent assistive patient support.

The patient table is configured to enable patient handling and positioning maneuvers governed by a desired kinetic and kinematic operation. The patient table is also configured to enable patient handling and positioning maneuvers in an adaptively assisted manner. The patient table includes a multi-layered patient support including a top layer configured to gradually transform between a flat bed and an upright-chair configuration to help patient handling and positioning. The multi-layered patient support also includes a bottom layer configured to physically engage with the top layer at certain times to help carry the patient (e.g., subject) in and out form an imaging gantry. The top and bottom layers are made of compatible materials (e.g., carbon fiber for CT, polycarbonate for MRI, etc.) to the imaging modality. The materials may be X-ray permeable.

The platform is configured to retain the multi-layered patient support at a desired elevation (e.g., height). The platform is also configured to linearly guide the top and bottom layers of the patient support in and out of the bore of the imaging gantry while selectively enabling or restricting relative movement between the two as determined by the patient handling and positioning requirement.

The mechanical coupling between the multi-layered patient support and the platform is configured to conditionally enable bidirectional vertical axis rotation and bidirectional tilting of the top layer of the patient support along with the patient as desired during the patient handling and positioning maneuvers. The patient table also includes a set of actuators (e.g., electromechanical actuators) and a collision avoidance system configured to be operated in tandem to help articulate the multi-layered patient support from time to time to derive various patient handling poses and spatial orientations relative to the coordinates of the imaging gantry.

The patient table also includes a set of sensors/encoders and a controller configured to gauge the kinetic and kinematic operation of the multi-layered patient support and accordingly drive the actuators to fulfill the needs of the patient support handling/positioning during various stages of the procedure. The set of sensors/encoders and the controller are also configured to gauge the patient's own efforts during ingress and egress, and intelligently and adaptively augment/supplement for any deficit through a programmatically carried out kinetic and kinematic operation of the elements of the assistive patient support to fulfill the needs of the patient handling/positioning during an imaging procedure. The patient table also includes hand rests (or arm rests) integrated with top layer of the multi-layered patient support that each includes a compliant hinge mechanism configured to ergonomically aid the patient during all patient handling maneuvers from time to time.

The kinetics and kinematics functioning of the patient positioner (of the patient table) provide for a controlled force and motion transmission across various connected elements of the patient support, thus producing an overall effect of an enhanced ergonomics for patient handling and positioning during an imaging procedure. The mechanical architecture is configured to enable gradual and conditional transformation of the patient support into various physically advantageous configurations (e.g., horizontal bed-lie setup, setup conducive for a zero-gravity position and an upright chair-like setup from time to time). The mechanical architecture is configured to enable smooth patient transfer in and out from the gantry bore, to enable head-first or feet-first flexibility for patient orientation during the imaging procedure (e.g., manually or programmatically), and enabling left- or right-sided patient loading and offloading for on-site procedures.

The controller and the set of sensors are configured to sense the patient-exerted effort at various elements and during ingress or egress attempts and to utilize a closed-loop feedback system to drive the operation of the set of actuators to collectively cause a desired adaptively-assisted articulation of the patient support for various patients depending on their severity of physical impairment or weakness. The intelligent collision and avoidance system is configured to sense and avoid imminent collision or patient fall on account of the articulation of the patient support inside the imaging room environment.

The disclosed embodiments enable overcoming physical challenges in patient handling and positioning during an imaging procedure while also enabling these tasks to be performed without necessitating additional staff. The articulating support is configured to assume various physically advantageous configurations to assist patient and staff through the patient loading, off-loading, and positioning maneuvers. The disclosed embodiments provide the flexibility of loading and off-loading the patient with equal ease from either side of the patient table to accommodate for site conditions.

The disclosed embodiments automatically adapt an articulating configuration to fulfill the assistive needs of various patients, rather than standardizing the articulated operation. The disclosed embodiments enable various articulating elements of the patient support to be selectively articulated (independent of other elements) for a certain extent of their travel while also enabling a concerted articulation of multiple elements in tandem, thereby progressively and effectively adapting to the patient's own effort to make the experience as natural as possible (while providing assistance during ingress or egress). The disclosed embodiments also eliminate any counter-assistive maneuvers of the articulating patient support that may be caused due to exceedingly high assistive force being generated or exerting less than effective assistive force depriving the patient of an assisted ingress or egress experience.

The disclosed embodiments provide an improved experience for imaging technologists/support staff relative to the laborious and time-consuming process of patient handling and positioning during imaging procedures. The disclosed embodiments increase throughput and eliminate the need for extra staff to assist with patient handling and positioning tasks. The disclosed embodiments provide an enhanced sense of empowerment, dignity, and safety for the patient.

With the preceding in mind and referring to FIG. 1, a computed tomography (CT) imaging system 10 is shown, by way of example. The CT imaging system 10 includes a gantry 12. The gantry 12 has an X-ray source 14 that projects a beam of X-rays 16 toward a detector assembly 15 on the opposite side of the gantry 12. The X-ray source 14 projects the beam of X-rays 16 through a pre-patient collimator assembly 13 that determines the size and shape of the beam of X-rays 16. The detector assembly 15 includes a collimator assembly 18 (a post-patient collimator assembly), a plurality of detector modules 20 (e.g., detector elements or sensors), and data acquisition systems (DAS) 32. The plurality of detector modules 20 detect the projected X-rays that pass through a subject or object 22 being imaged, and DAS 32 converts the data into digital signals for subsequent processing. Each detector module 20 in a conventional system produces an analog electrical signal that represents the intensity of an incident X-ray beam and hence the attenuated beam as it passes through the subject or object 22. During a scan to acquire X-ray projection data, gantry 12 and the components mounted thereon rotate about a center of rotation 25 (e.g., isocenter) so as to collect attenuation data from a plurality of view angles relative to the imaged volume.

Rotation of gantry 12 and the operation of X-ray source 14 are governed by a control system 26 of CT imaging system 10. Control system 26 includes an X-ray controller 28 that provides power and timing signals to an X-ray source 14, a collimator controller 29 that controls a length and a width of an aperture of the pre-patient collimator 13 (and, thus, the size and shape of the beam of X-rays 16), and a gantry motor controller 30 that controls the rotational speed and position of gantry 12. An image reconstructor 34 receives sampled and digitized X-ray data from DAS 32 and performs high-speed image reconstruction. The reconstructed image is applied as an input to a computer 36, which stores the image in a storage device 38. Computer 36 also receives commands and scanning parameters from an operator via console 40. An associated display 42 allows the operator to observe the reconstructed image and other data from computer 36. The operator supplied commands and parameters are used by computer 36 to provide control signals and information to DAS 32, X-ray controller 28, collimator controller 29, and gantry motor controller 30. In addition, computer 36 operates a table motor controller 44, which controls a motorized table 46 (e.g., patient table) to position subject 22 and gantry 12. Particularly, table 46 moves portions of subject 22 through a gantry opening or bore 48.

The table motor controller 44 (and/or the computer 36) includes a memory a processing system including one or more processors to execute instructions stored in the memory. The table motor controller 44 is communicatively coupled to actuators 50 coupled to table 46 (including multi-layered patient support). The actuators 50 may include electromechanical actuators (e.g., rotary and/or linear), hydraulic actuators, pneumatic actuators, springs, gas springs, or other types of actuators. The table motor controller 44 is communicatively coupled to a first set of sensors 52 coupled to the table 46 (including multi-layered patient support). The table motor controller 44 is configured to control movements of the table 46 and/or an articulating patient support (via control signals sent to the actuators 50) based on feedback from the sensors 52. In particular, the table motor controller 44 is configured to receive feedback from the first set of sensors 52, to estimate both a subject's pose and exerted physical effort towards either ingress into or egress from the top patient support based on the feedback, to calculate respective assistive forces needed at various portions of the top patient support based on the subject's pose and exerted physical effort, and to provide control signals to the plurality of actuators 50 to deliver the respective assistive forces at the various portions of the top patient support. The sensors 52 may include pressure sensors, strain gauges, linear/rotary encoders, or other sensors embedded within an articulating patient support or elements thereof. The table motor controller 44 is also communicatively coupled to one or more additional sensors 54 and/or a camera 56. The additional sensors 54 may include electromagnetic sensors and/or optical sensors. The additional sensors 54 and/or the camera 56 along with the table motor controller 44 are configured to act an intelligent collision and avoidance system 58. The table motor controller 44 is configured to receive feedback from the sensors 54 and/or the camera to sense and to avoid imminent collision or patient falls on account of the articulation of the patient support inside the imaging room environment. In particular, the table motor controller 44 is configured to receive additional feedback from the one or more additional sensors 54 and to provide control signals, based on the additional feedback, to the plurality of actuators 50 to keep the subject from colliding with an object within a room that the medical imaging system 10 is disposed within and/or to keep the subject from falling from the multi-layered patient support. The sensors 54 and/or the camera 56 may be coupled to the articulating patient support, table 46, or other component of the imaging system 10 (e.g., gantry 12). In certain embodiments, the camera 56 may not be coupled to the imaging system 10 but disposed in another location within the imaging room.

Although the patient table 46 in the present disclosure is discussed in the context of a CT imaging system, the patient table 46 may be utilized with other types of medical imaging systems (e.g., magnetic resonance imaging system, nuclear medicine imaging system, etc.). That is, the depicted example of the CT imaging system 10 is merely one environment in which the described patient table 46 may be implemented. Aspects of the patient table 46 in the following figures are discussed utilizing a coordinate system having a y-direction (or y-axis), an x-direction (or x-axis), and a z-direction (or z-axis). The coordinate system may be discussed relative to a longitudinal axis of the patient table 46 (and its patient support (e.g., cradle)).

Figure 2:
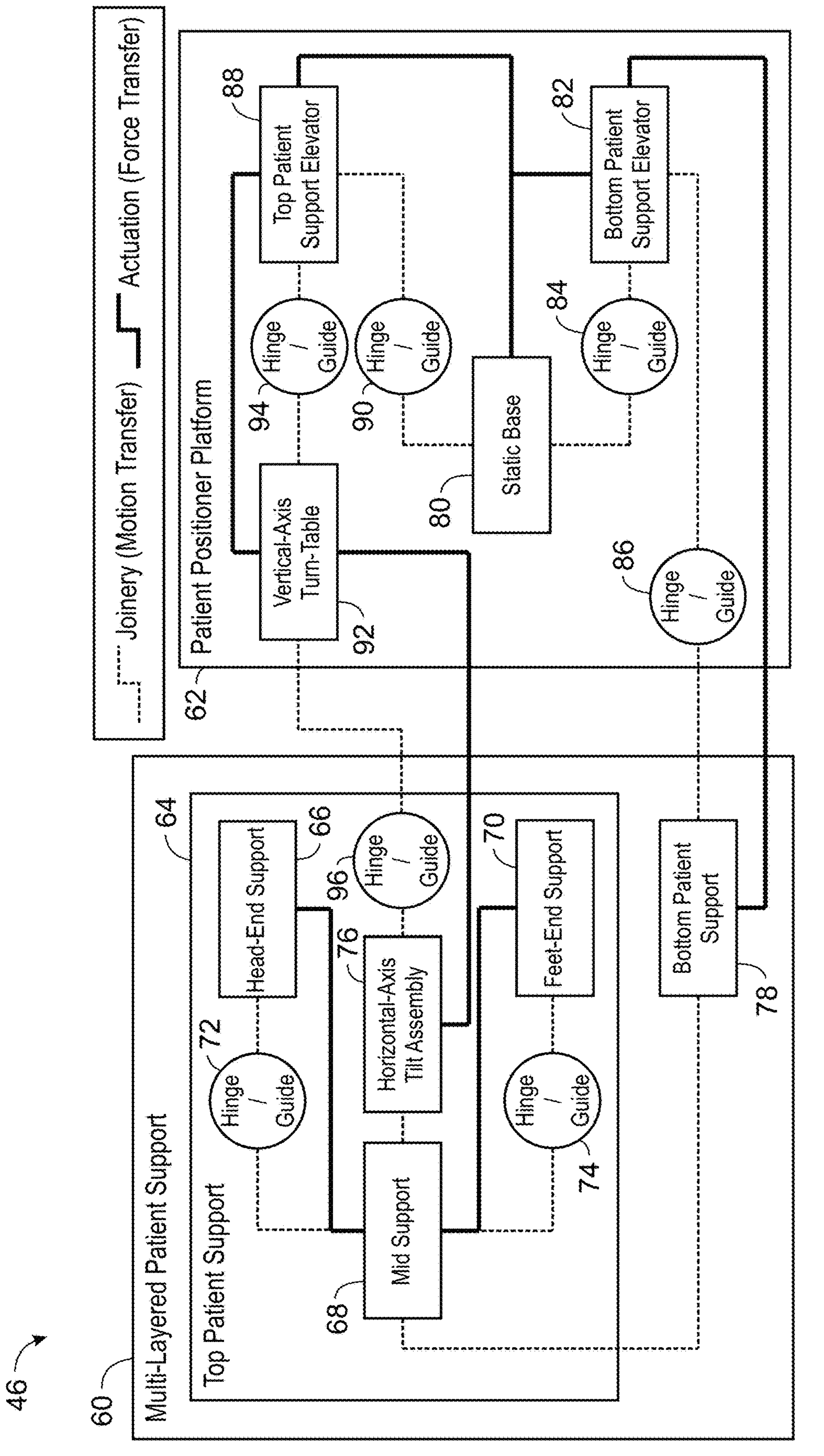
FIG. 2 is a schematic diagram of an architecture (e.g., kinetics and kinematics) of a patient table, in accordance with aspects of the present disclosure.

FIG. 2 is a schematic diagram of an architecture (e.g., kinetics and kinematics) of the patient table 46. Solid lines indicate joinery (i.e., motion transfer) and dashed lines indicate actuation (i.e., force transfer). Actuation of components of the patient table 46 may occur via control signals sent from a controller (e.g., table motor controller 44 in FIG. 1) to actuators (e.g., actuator 50 in FIG. 1).

The patient table 46 includes a multi-layered patient support 60 (e.g., cradle) and a patient positioner platform 62. The multi-layered patient support 60 is configured to support a patient (e.g., subject) during an imaging procedure. The multi-layered patient support 60 includes a top patient support 64 (e.g., top layer). The top patient support 64 includes multiple segments that articulate with respect to each other to form different configurations. For example, the top patient support 64 is configured to be in a first configuration where the top patient support 64 is flat and horizontal to support the subject in a recumbent position. The top patient support 64 is configured to be in a second configuration where the top patient support 64 is in an upright-chair configuration to support the subject in an upright seated position. The top patient support 64 is also configured to be in a third configuration in a transition between the first configuration and the second configuration, wherein in the third configuration the top patient support 64 is configured to support the subject in a zero-gravity position (i.e., subject seated or laying in an inclined position with feet elevated). The top patient support 64 is also configured to be in a fourth position where the top patient support 64 is perpendicular to a longitudinal axis of the patient positioner platform 62, located on a lateral side of the patient positioner platform (left or right side relative to the longitudinal axis), and the surface of the top patient support 64 that interfaces with the patient faces away from the patient positioner platform 62. The top patient support 64 is in the fourth configuration during the egress or ingress of the patient on the top patient support 64.

The top patient support 64 includes a head-end support section 66, a mid-support section 68, and a feet-end support section 70 (with section 68 located between the sections 66 and 70). Each of these sections 66, 68, and 70 may be associated with a respective support. The head-end support section 66 is coupled to the mid-support section 68 via a hinge/guide 72. The mid-support section 68 is coupled to the feet-end support section 70 via a hinge/guide 74. The hinges/guides 72, 74 enable articulation between the different sections 66, 68, 70. In certain embodiments, the top patient support 64 may include an additional support section (see FIG. 15) coupled to the feed-end support section 70 that serves as a footrest that articulates through various configurations during the patient support articulation.

The mid-support section 68 is coupled to a horizontal-axis tilt assembly 76. The horizontal-axis tilt assembly 76 is configured to bi-directionally tilt the top patient support 64. For example, the horizontal-axis tilt assembly 76 is configured to tilt the top patient support 64 to move to the third configuration in a transition between the first configuration and the second configuration. The horizontal-axis tilt assembly 76 is configured to tilt the top patient support 64 from the third configuration to either the first configuration or the second configuration. The horizontal-axis tilt assembly 76 is configured to tilt the top patient support 64 to move between the second configuration and the fourth configuration.

The multi-layered patient support 60 also includes a bottom patient support 78 (e.g., bottom layer). The bottom patient support 78 is configured to engage the top patient support 64 at certain points. For example, the bottom patient support 78 is configured to engage the top patient support 64 when in the first configuration. In the first configuration, the top patient support 64 and the bottom patient support 78 are configured to act together to move the patient in and out of the bore of a gantry during an imaging procedure.

The patient positioner platform 62 includes a static base 80 (e.g., fixed base). The rest of the patient positioner platform 62 is configured to move (e.g., vertically) relative to the static base 80. The patient positioner platform 62 is coupled to a bottom patient support elevator 82 (e.g., bottom patient vertical lift) via a hinge/guide 84. The bottom patient support elevator 82 is coupled to the bottom patient support 78 via hinge/guide 86. The bottom patient support elevator 82 is configured to move the bottom patient support 78 up and down vertically relative to the static base 80.

The patient positioner platform 62 is coupled to a top patient support elevator 88 (e.g., top patient vertical lift) via hinge/guide 90. The top patient support elevator 88 is coupled to a vertical axis turn-table 92 via hinge/guide 94. The vertical axis turn-table 92 is coupled to the horizontal axis tilt assembly 76 (and the top patient support 64) via hinge guide 96. The top patient support elevator 88 is configured to move the top patient support 64 and the vertical axis turn-table 92 up and down vertically relative to the static base 80. The vertical axis turn-table 92 is configured to rotate the top patient support 64 about a vertical axis. In particular, the vertical axis turn-table 92 is configured, when the top patient support is in the third configuration, to rotate the top patient support 64 about the vertical axis during the transition between the first configuration and the second configuration. The vertical axis turn-table 92 is configured, when the top patient support 64 is in the third configuration, is configured to rotate the top patient support 64 between a first orientation (in the first configuration) where the patient faces away from the patient table 46 and a second orientation where the patient faces toward a longitudinal end of the patient table 46 (prior to transition from third configuration to the first configuration or prior to the transition from third configuration to the second configuration).

Figure 3:
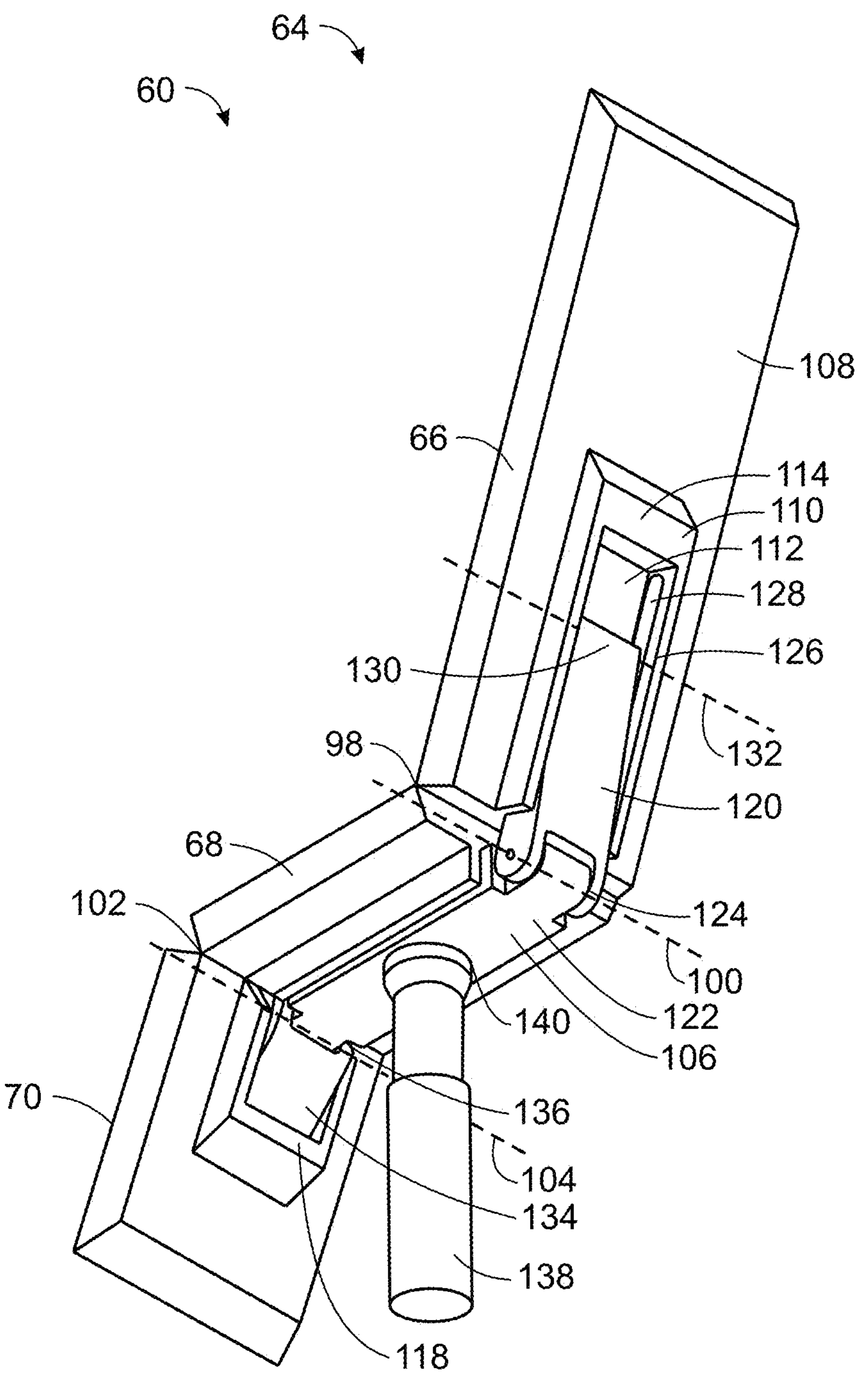
FIG. 3 is a perspective view of a top patient support of a multi-layered patient support, in accordance with aspects of the present disclosure.

FIG. 3 is a perspective view of the top patient support 64 of the multi-layered patient support 60. As depicted, the top patient support 64 is in an upright-chair configuration (i.e., the second configuration). The top patient support 64 includes the head-end support section 66, the mid-support section 68, and the feet-end support section 70. The top patient support 64 also includes a compliant hinge 98 configured to enable the head-end support section 66 and the mid-support section 68 to rotate with respect to each other about axis 100. The top patient support 64 also includes a compliant hinge 102 configured to enable the mid-support support section 68 and the feet-end support section 70 to rotate with respect to each other about axis 104.

A mechanical support system 106 is coupled to the top patient support 64. The mechanical support system 106 is configured to support and to alter the positions of the sections 66, 68, 70 relative to each other to put the top patient support 64 into the desired configuration. Each bottom surface 108 of the sections 66, 68, 70 form a structure 110 having a recess 112 to receive the mechanical support system 106. The sections 66, 68, 70 include respective structure sections 114, 116, and 118 that form the structure 110.

The mechanical support system 106 includes a top section mechanical support 120 associated with the head-end support section 66 and disposed within the recess 112 of the structure section 114. The mechanical support system 106 includes a tabletop carrier 122 (e.g., middle section mechanical support) associated with the mid-support section 68 and disposed within the recess 112 of the structure section 116. The tabletop carrier 122 is pivotally coupled to the top section mechanical support 120. A rotary actuator 124 is configured to rotate the top section mechanical support 120 relative to the tabletop carrier 122 and, thus, rotate the head-end support section 66 relative to the mid-support section 68 about the axis 100. During rotation of the top section mechanical support 120 relative to the tabletop carrier 122, the top section mechanical support 120 slides within the recess 112 of the structure section 114 via hinge pins 126 (coupled to the top section mechanical support 120) disposed within a linear guide 128 of the structure section 114. During rotation of the top section mechanical support 120 relative to the tabletop carrier 122, an end 130 of the top section mechanical support 120 and the head-end support section 66 rotate relative to each other about axis 132.

The mechanical support system 106 includes a leg section mechanical support 134 associated with the feet-end support section 70 and disposed within the recess 112 of the structure section 118. The tabletop carrier 122 is pivotally coupled to the leg section mechanical support 134. A rotary actuator 136 is configured to rotate the leg section mechanical support 134 relative to the tabletop carrier 122 and, thus, rotate the feet-end support section 70 relative to the mid-support section 68 about the axis 104.

As depicted, the mechanical support system 106 is coupled to a telescopic column 138 via a dovetail docking 140 (e.g., during the second, third, and fourth configurations). In certain embodiments (i.e., certain configurations such as the first configuration of the top patient support 64), the telescopic column 138 is decoupled from the top patient support 64).

Figure 4:
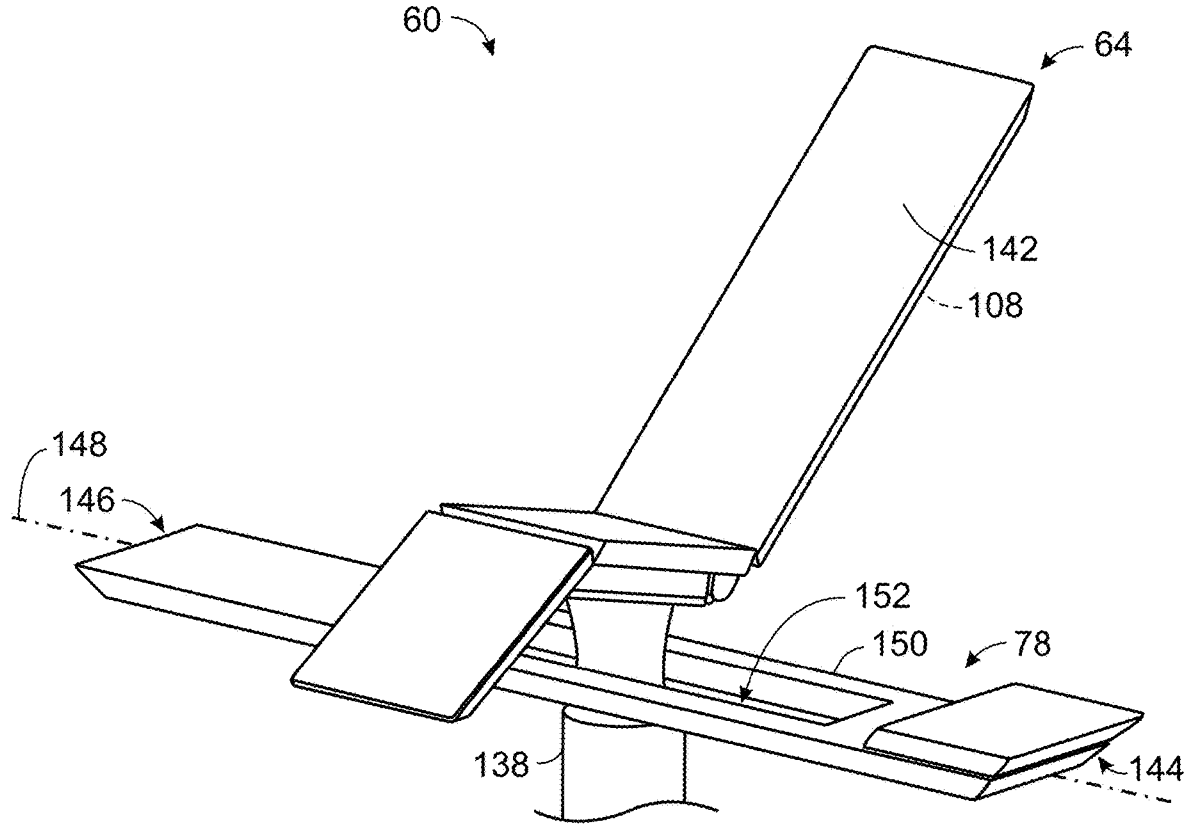
FIG. 4 is a perspective view of a multi-layered patient support, in accordance with aspects of the present disclosure.

FIG. 4 is a perspective view of the multi-layered patient support 60. The top patient support 64 is as described in FIG. 3. As depicted, the top patient support 64 is in a zero-gravity configuration (i.e., the third configuration). The multi-layered patient support 60 also includes the bottom patient support 78. In third configuration, the bottom patient support 78 does not physically engage the top patient support 64. A surface 142 of the top patient support 64 that interfaces with the patient is facing away from longitudinal ends 144, 146 of the bottom patient support. In transitioning to the first configuration, the top patient support 64 is rotated toward the longitudinal end 144 so that the surface 142 faces the longitudinal end 144 so that the top patient support 64 is axially aligned with a longitudinal axis 148 of the bottom patient support 78. Rotation may may occur from the left side or the right side relative to the longitudinal axis 148 of the bottom patient support 78. Then top patient support 64 is actuated to the first configuration where the top patient support 64 is flat and horizontal extending along the longitudinal axis 148 so that the bottom surface 108 of the top patient support 64 physically engages with a top surface 150 of the bottom patient support 78. In the first configuration, the head-end support section 66 and the feet-end support section 70 are disposed adjacent the longitudinal ends 146, 144, respectively.

As depicted, the telescopic column 138 is coupled to the top patient support 64. The telescopic column 138 is disposed within and extends through an opening 152 in the bottom patient support 78. The telescopic column 138 is decoupled from the top patient support 64 when the top patient support is in the first configuration.

Figures 5A, 5B, 5C, 5D, 5E, 5F, 5G, 5H:
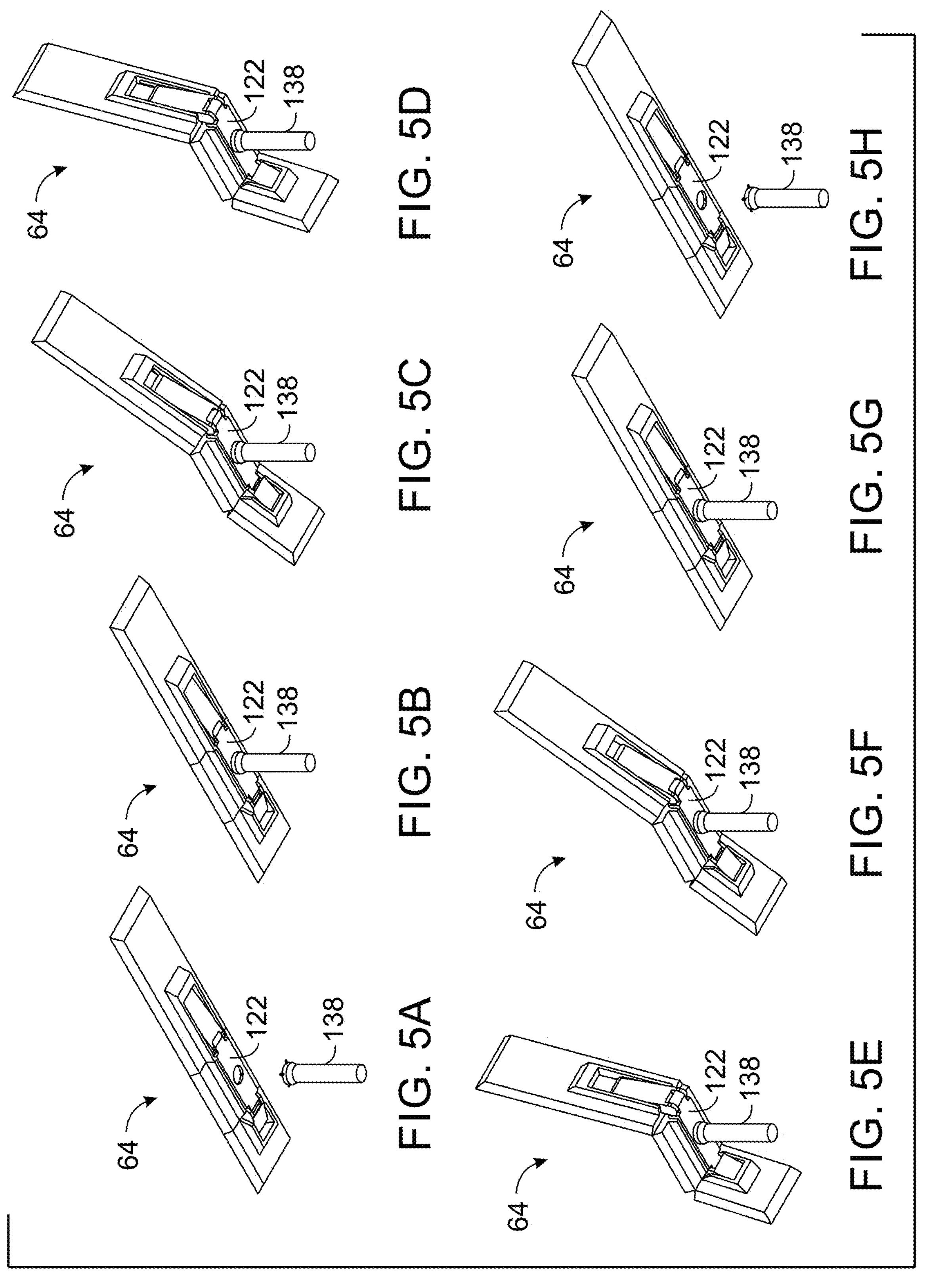
FIGS. 5A-5H are schematic diagrams illustrating docking with the top patient support of the multi-layered patient support in FIG. 3, in accordance with aspects of the present disclosure.

Docking with the top patient support 64 may occur in different ways. FIGS. 5A-5H are schematic diagrams illustrating docking with the top patient support 64 of the multi-layered patient support in FIG. 3. In FIG. 5A, the top patient support 64 is in the first configuration (flat and horizontal) and the telescopic column 138 is decoupled from the tabletop carrier 122 of the mechanical support system 106. In FIG. 5B, the telescopic column 138 is coupled to the tabletop carrier 122 and thus coupled to the top patient support 64 in the first configuration. In FIG. 5C, while the telescopic column 138 is coupled to the tabletop carrier 122, the top patient support 64 has transitioned to the third configuration (zero-gravity configuration). In FIG. 5D and FIG. 5E, while the telescopic column 138 is coupled to the tabletop carrier 122, the top patient support 64 transitions from the third configuration to the second configuration (upright-chair configuration). In FIG. 5F, while the telescopic column 138 is coupled to the tabletop carrier 122, the top patient support 64 transitions from the second configuration back to the third configuration. In FIG. 5G, while the telescopic column 138 is coupled to the tabletop carrier 122, the top patient support 64 transitions from the third configuration to the first configuration. In FIG. 5H, while the top patient support 64 is in the first configuration, the telescopic column 138 decouples from the tabletop carrier 122.

Figures 6A, 6B, 6C, 6D, 6E, 6F, 6G, 6H:
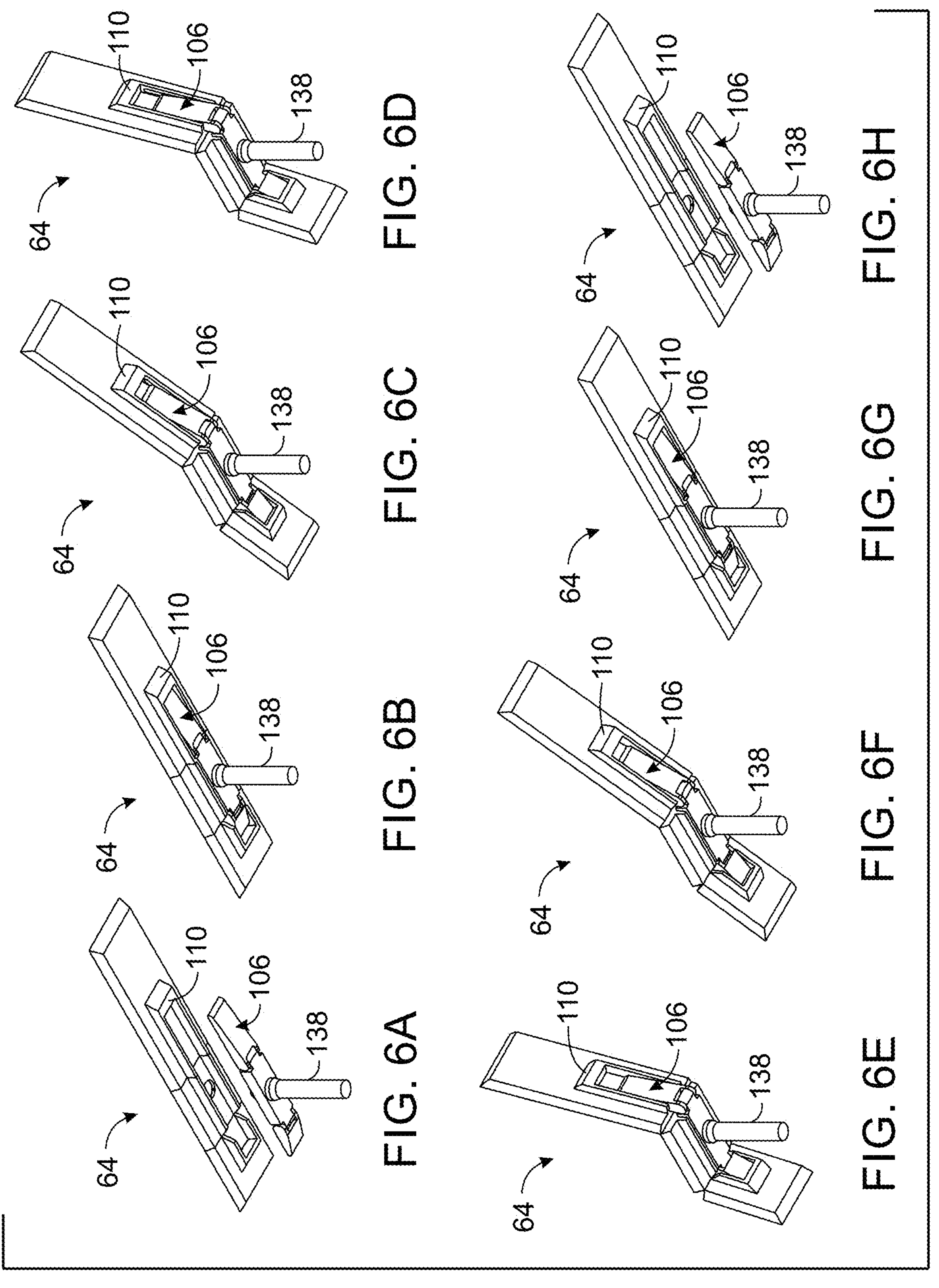
FIGS. 6A-6H are schematic diagrams illustrating alternative docking with the top patient support of the multi-layered patient support in FIG. 3, in accordance with aspects of the present disclosure.

FIGS. 6A-6H are schematic diagrams illustrating alternative docking with the top patient support 64 of the multi-layered patient support in FIG. 3. In FIG. 6A, the top patient support 64 is in the first configuration (flat and horizontal) and both the telescopic column 138 and the mechanical support system 106 (which are coupled together) are decoupled from the structure 110 (and, thus, decoupled from the top patient support 64). In FIG. 6B, both the telescopic column 138 and the mechanical support system 106 are coupled to the structure 110 and thus coupled the top patient support 64 in the first configuration. In FIG. 6C, while both the mechanical support system 106 and the telescopic column 138 are coupled to the structure 110, the top patient support 64 has transitioned to the third configuration (zero-gravity configuration). In FIG. 6D and FIG. 6E, while both the mechanical support system 106 and the telescopic column 138 are coupled to the structure 110, the top patient support 64 transitions from the third configuration to the second configuration (upright-chair configuration). In FIG. 6F, while both the mechanical support system 106 and the telescopic column 138 are coupled to the structure 110, the top patient support 64 transitions from the second configuration back to the third configuration. In FIG. 6G, while both the mechanical support system 106 and the telescopic column 138 are coupled to the structure 110, the top patient support 64 transitions from the third configuration to the first configuration. In FIG. 6H, while the top patient support 64 is in the first configuration, both the mechanical support system and the telescopic column 138 (while remaining coupled together) decouple from the structure 110.

Figure 7:
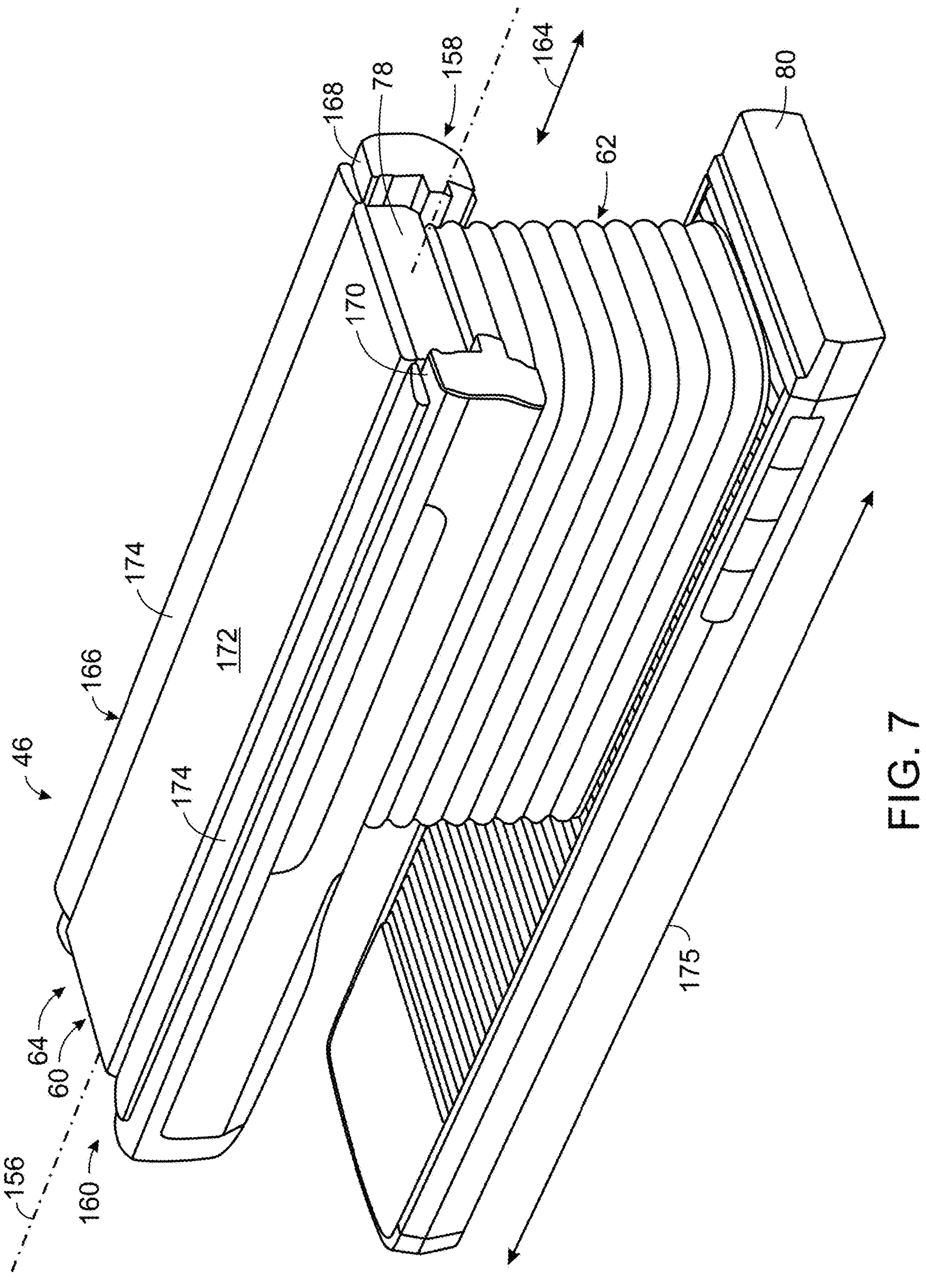
FIG. 7 is a perspective view of the patient table with a top patient support in a first configuration (i.e., flat and horizontal configuration), in accordance with aspects of the present disclosure.
Figure 8:
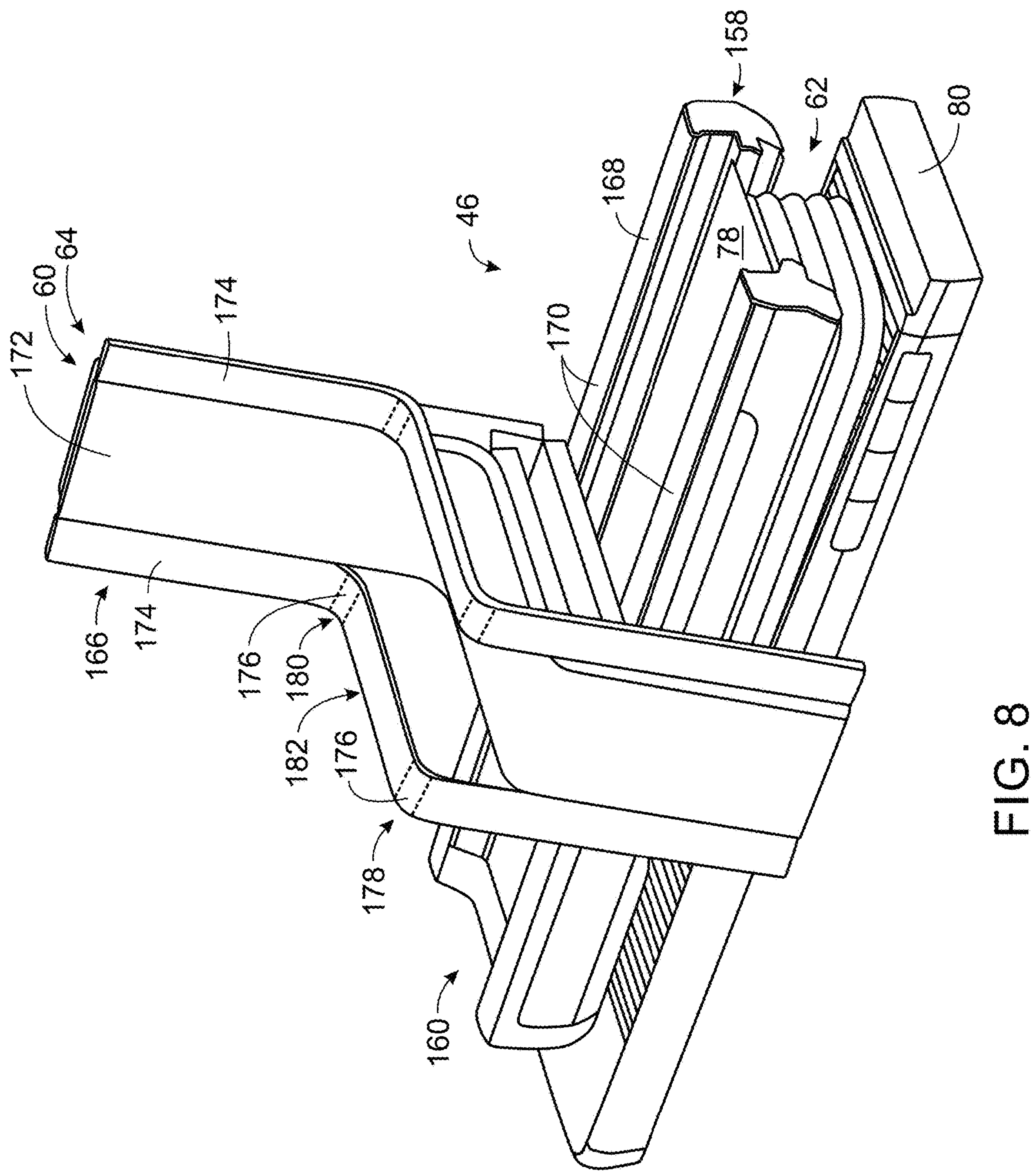
FIG. 8 is a perspective view of the patient table in FIG. 7 with the top patient support in a second configuration (i.e., upright-chair configuration), in accordance with aspects of the present disclosure.
Figure 9:
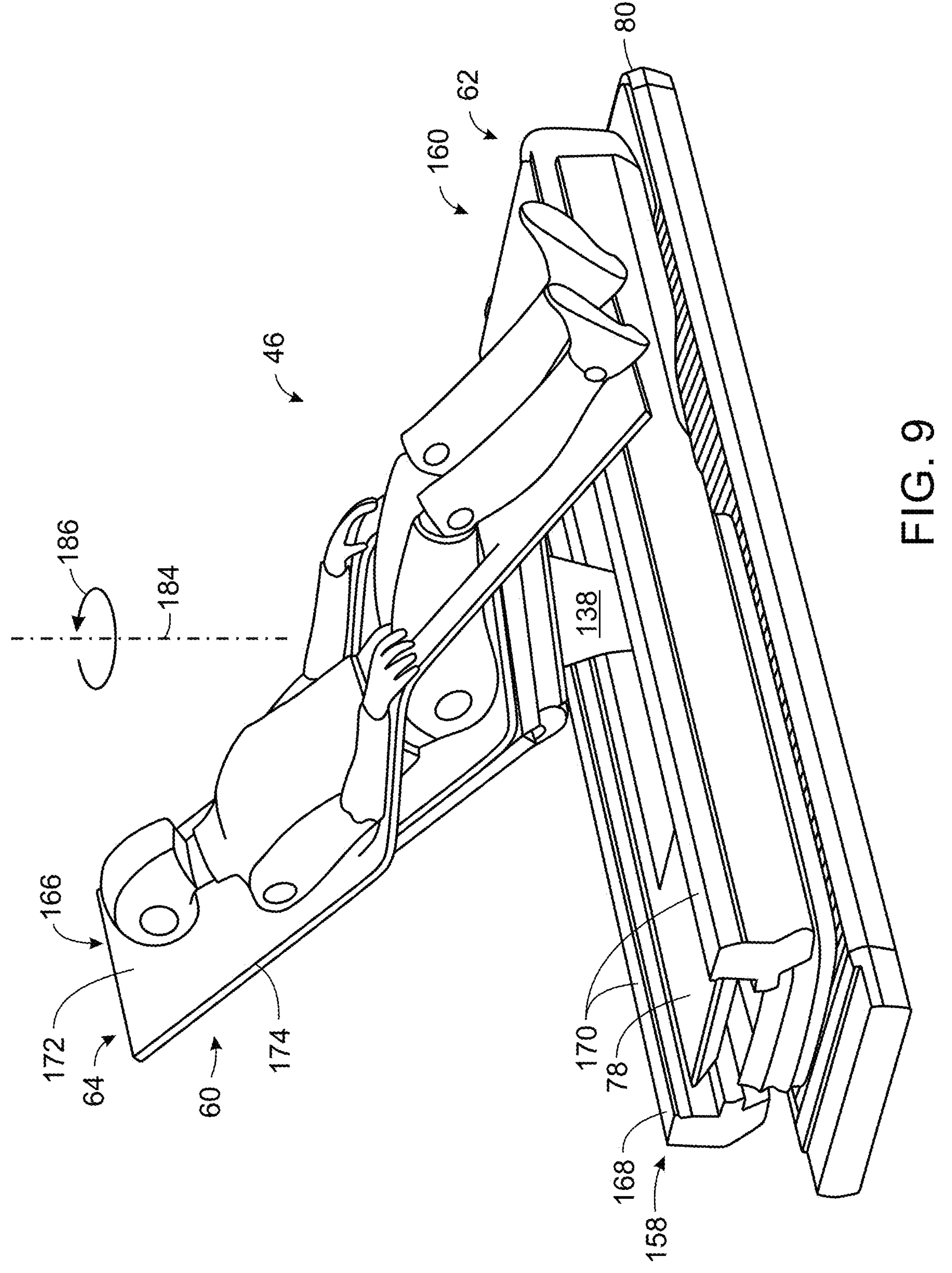
FIG. 9 is a perspective view of the patient table in FIG. 7 with the top patient support in a third configuration (i.e., zero-gravity configuration), in accordance with aspects of the present disclosure.
Figure 10:
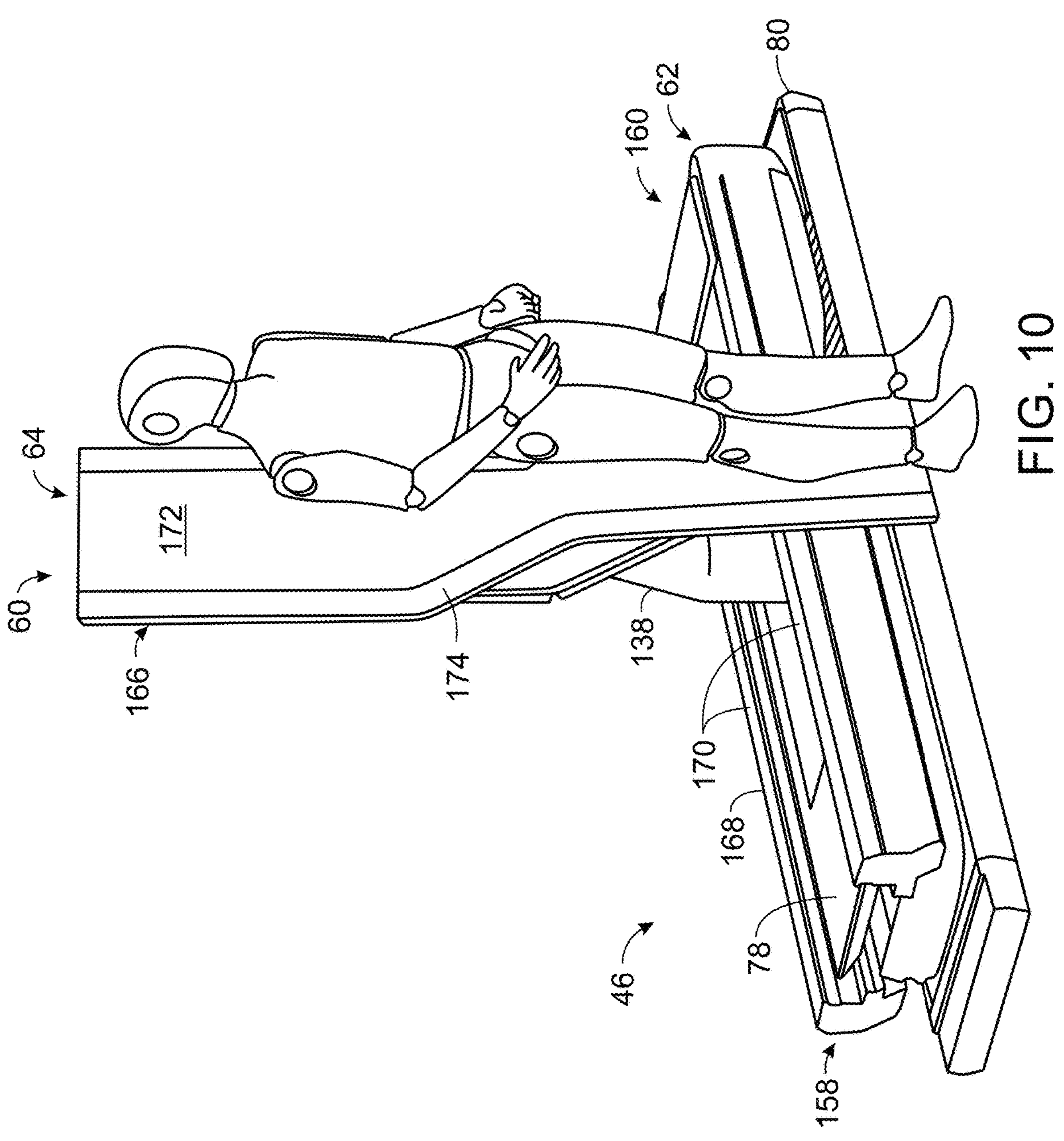
FIG. 10 is a perspective view of the patient table in FIG. 7 with the top patient support in a fourth configuration (i.e., vertical configuration), in accordance with aspects of the present disclosure.

FIGS. 7-10 are perspective views of the patient table 46 with the top patient support 64 in different configurations. In FIG. 7, the top patient support 64 is in a first configuration (i.e., flat and horizontal configuration). In FIG. 8, the top patient support 64 is in a second configuration (i.e., upright chair configuration). In FIG. 9, the top patient support 64 is in a third configuration (i.e., zero-gravity configuration). In FIG. 10, the top patient support 64 is in a fourth configuration (i.e., vertical configuration).

As depicted, the patient table 46 includes the multi-layered patient support 60 having the top patient support 64 and the bottom patient support 78. The patient table 46 also includes the patient positioner platform 62. The patient positioner platform 62 is coupled to the static base 80. The patient positioner platform 62 is configured to move bidirectionally in a vertical direction 154 relative to the static base 80. As depicted in FIGS. 8-10, the patient positioner platform 62 is lowered toward the static base 80 to enable rotation and tilting of the top patient support 64. In the first configuration in FIG. 7, the patient positioner platform 62 is raised relative to the static base 80. The patient table 46 includes a longitudinal axis 156 and has longitudinal ends 158, 160. Longitudinal end 158 is adjacent to a patient's head and longitudinal end 160 is adjacent to patient's feet when the patient 162 is laying down on the multi-layered patient support 60.

In FIGS. 7-10, the bottom patient support 78 is disposed within the patient positioner platform 62. In FIG. 7, the bottom patient support 78 is physically engaged with the top patient support 64 and top patient support 64 is decoupled from any vertical lift. Both the top patient support 64 and the bottom patient support 78 acting together (as the multi-layered patient support 60) are configured to move the patient 162 into and out of a bore of a gantry of an imaging system during an imaging procedure. In particular, the multi-layered patient support 60 is configured to extend from and move back toward the longitudinal end 158 of the patient positioner platform 62 as indicated by arrow 164. The patient positioner platform 62 is configured to maintain an elevation (e.g., height) of the multi-layered patient support 60. In FIGS. 8-10, the bottom patient support 78 is not physically engaged with the top patient support 64, while the top patient support is 64 is coupled to the column 138 (and a vertical lift and tilting and rotating assemblies).

In FIGS. 7-10, the top patient support 64 includes a patient interfacing layer 166 disposed on top to interface with the patient 162. In FIG. 7, the front-end support section, mid-support section, and the feet-end support section of the top patient support 64 are disposed within and below a top surface 168 of the patient positioner platform 62, while the patient interfacing layer 166 is disposed above the top surface 168. The patient positioner platform 62 includes rails 170 that flank the front-end support section, mid-support section, and the feet-end support section of the top patient support 64 when disposed within the patient platform. The rails 170 act as guides as the multi-layered patient support 60 extends from and moves back toward the patient positioner platform 62.

The patient interfacing layer 166 includes a central portion 172 and hand rests 174 (or arm rests) flanking the central portion 172. Both the central portion 172 and the hand rests 174 extend an entire length 175 of the patient interfacing layer 166. The hand rests 174 move with the patient 162 between the different configurations. Each hand rest 174 includes hinge mechanisms 176 (disposed within) that are configured to enable the hand rest 174 to flex at two locations 178, 180 (as depicted in FIGS. 8-10) to move a portion 182 of the hand rest 174 away from the central portion 172 when transitioning to the second configuration and to move the portion of the hand rest 174 toward the central portion 172 when transitioning to the first configuration. In the second, third, and fourth configurations, the portion 182 of the hand rests 174 are separate from (i.e., located away) from the central portion 172. In the first configuration, the hand rests 174 are located above and parallel with the rails 170.

As depicted in FIGS. 8-10, the top patient support 64 may be tilted (bidirectionally) to different degrees in the second, third, and fourth configurations. In addition, the top patient support 64 may be raised. As depicted in FIGS. 8-10, the patient interfacing layer 166 is rotated toward a side of the patient positioner platform 62 and faces away from the patient positioner platform 62. In FIG. 10, the top patient support 64 is extended vertically relative to the longitudinal axis 156 of the patient table 46 to enable ingress or egress of the patient 162. In the third configuration depicted in FIG. 9, the top patient support 64 and the patient 162 may be rotated about a vertical axis 184 as indicated by arrow 186 for transition from the third configuration to the first configuration or transition from the third configuration to the second configuration.

Figure 11:
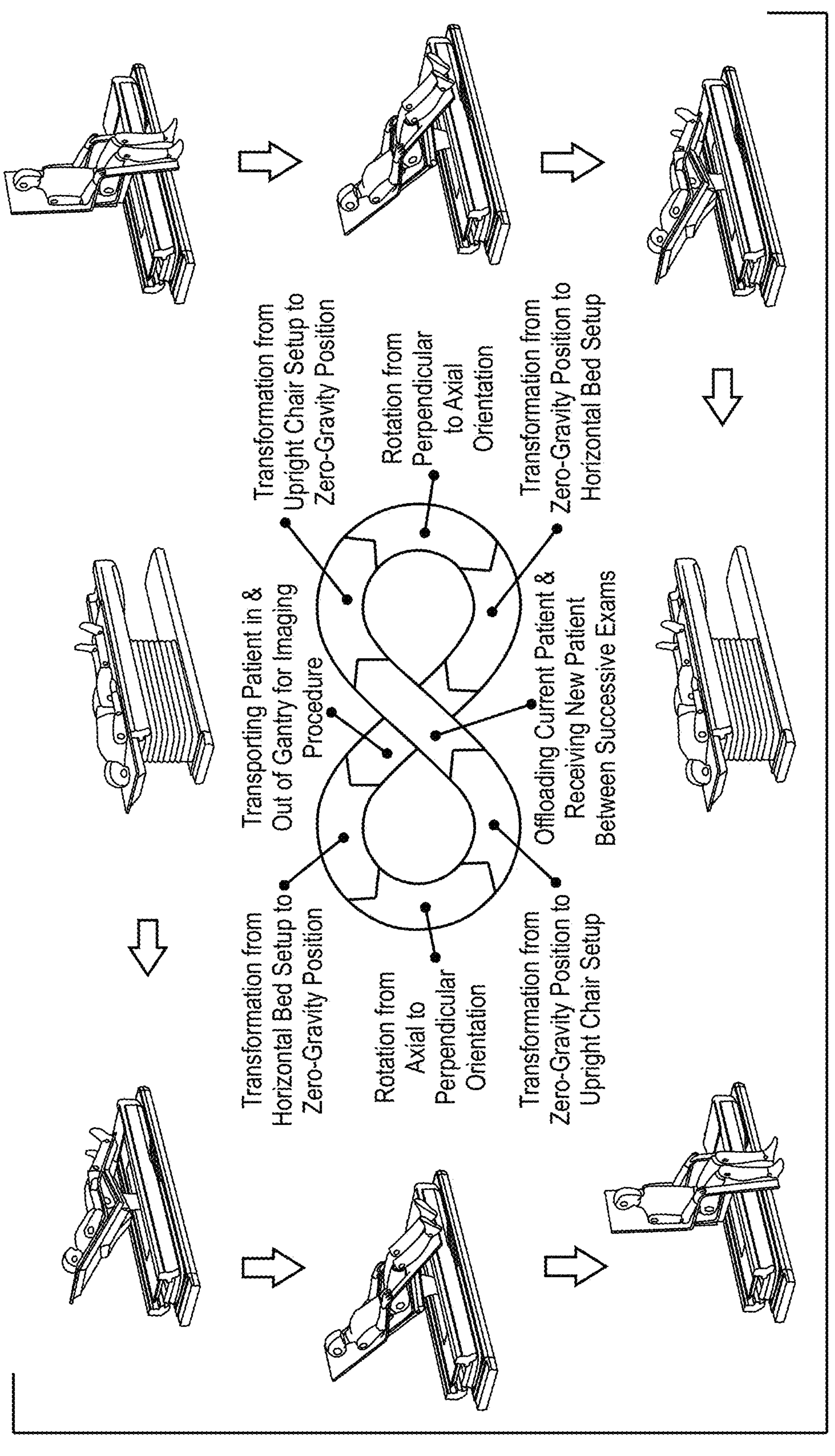
FIG. 11 is a schematic diagram illustrating the transition between the different configurations for the top patient support, in accordance with aspects of the present disclosure.

FIG. 11 is a schematic diagram illustrating the transition between the different configurations for the top patient support of the top patient support 64 of the patient table 46. The left side of FIG. 11 depicts the transition from the first configuration to the second configuration. In the first configuration, as indicated by reference numeral 188, the top patient support 64 is flat and horizontal and supporting the patient 162 in a recumbent position. As depicted in the first configuration, the patient positioner platform 62 is raised. The top patient support 64 then transitions to the third configuration (zero-gravity configuration), as indicated by reference numeral 190. In the third configuration (as well as the second configuration), the patient positioner platform 62 is lowered. The top patient support 64 is then rotated toward a side of the patient positioner platform 62 so that the patient 162 is facing away from the patient positioner platform 62 as indicated by reference numeral 192. The top patient support 64 then transitions to the second configuration (upright-chair configuration), via tilting, to put the patient 162 in an upright-seated position as indicated by reference numeral 194.

Figure 12:
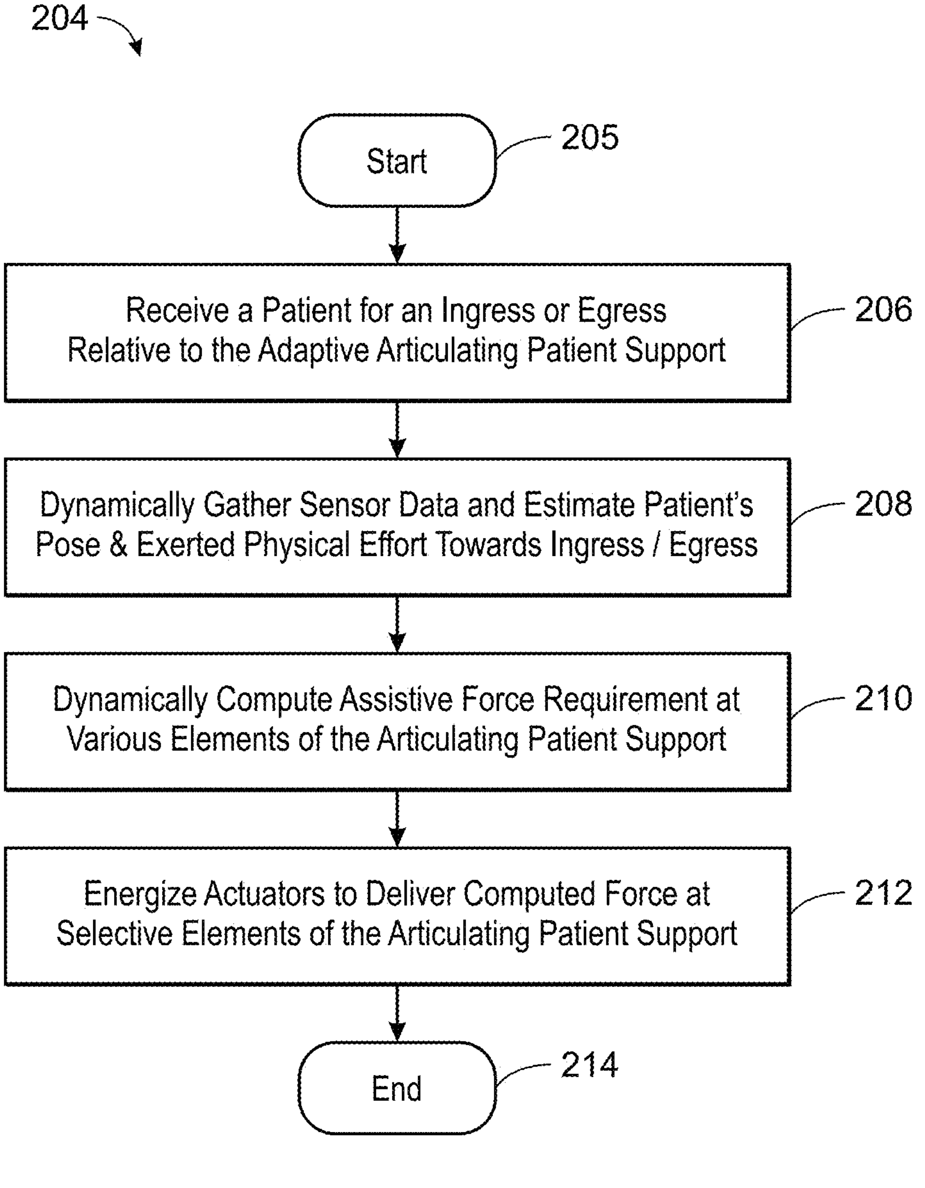
FIG. 12 is a flow chart of a method for providing adaptively assistive support to a patient utilizing an articulating patient support, in accordance with aspects of the present disclosure.

The right side of FIG. 12 depicts the transition from the second configuration to the first configuration. In the second configuration, as indicated by reference numeral 196, the top patient support 64 is in the second configuration with the patient in the upright-seated position. In the second configuration (as well as the third configuration), the patient positioner platform 62 is lowered. The top patient support 64 then transitions from the second configuration to the third configuration (via tilting) as indicated by reference numeral 198. The top patient support 64 is then rotated to face toward a longitudinal end of the patient positioner platform as indicated by reference numeral 200. The top patient support 64 then transitions to first configuration, as indicated by reference numeral 202, to support the patient in the recumbent position. The patient positioner platform 62 also is raised.

FIG. 12 is a flow chart of a method 204 for providing adaptively assistive support to a patient utilizing an articulating patient support. One or more steps of the method 204 may be performed by one or more components of the patient table 46 in FIG. 2 and/or table motor controller 44 in FIG. 1.

The method 204 includes, upon staring (block 205) receiving a patient for an ingress or egress relative to an adaptive articulating patient support (e.g., the top patient support 64 in FIG. 2) (block 206). The method 204 also includes dynamically gathering (e.g., receiving) sensor data or feedback (e.g., from sensors 52 in FIG. 1) and estimating the patient's pose and exerted physical effort towards ingress/egress (block 208). The method 204 further includes dynamically computing or calculating an assistive force requirement at various elements (e.g., portions) of the articulating patient support (block 210). The assistive force is calculated as a vector (i.e., amount plus direction) based on whether the assistive force is for ingress or egress. The method 204 even further includes energizing actuators (e.g., actuators 50 in FIG. 1), via control signals provided by a controller, to deliver computed force at selective elements of the articulating patient support (block 212), whereupon the method 204 ends (block 214). Control of the adaptively assisted support utilizes a closed-loop feedback.

Figure 13:
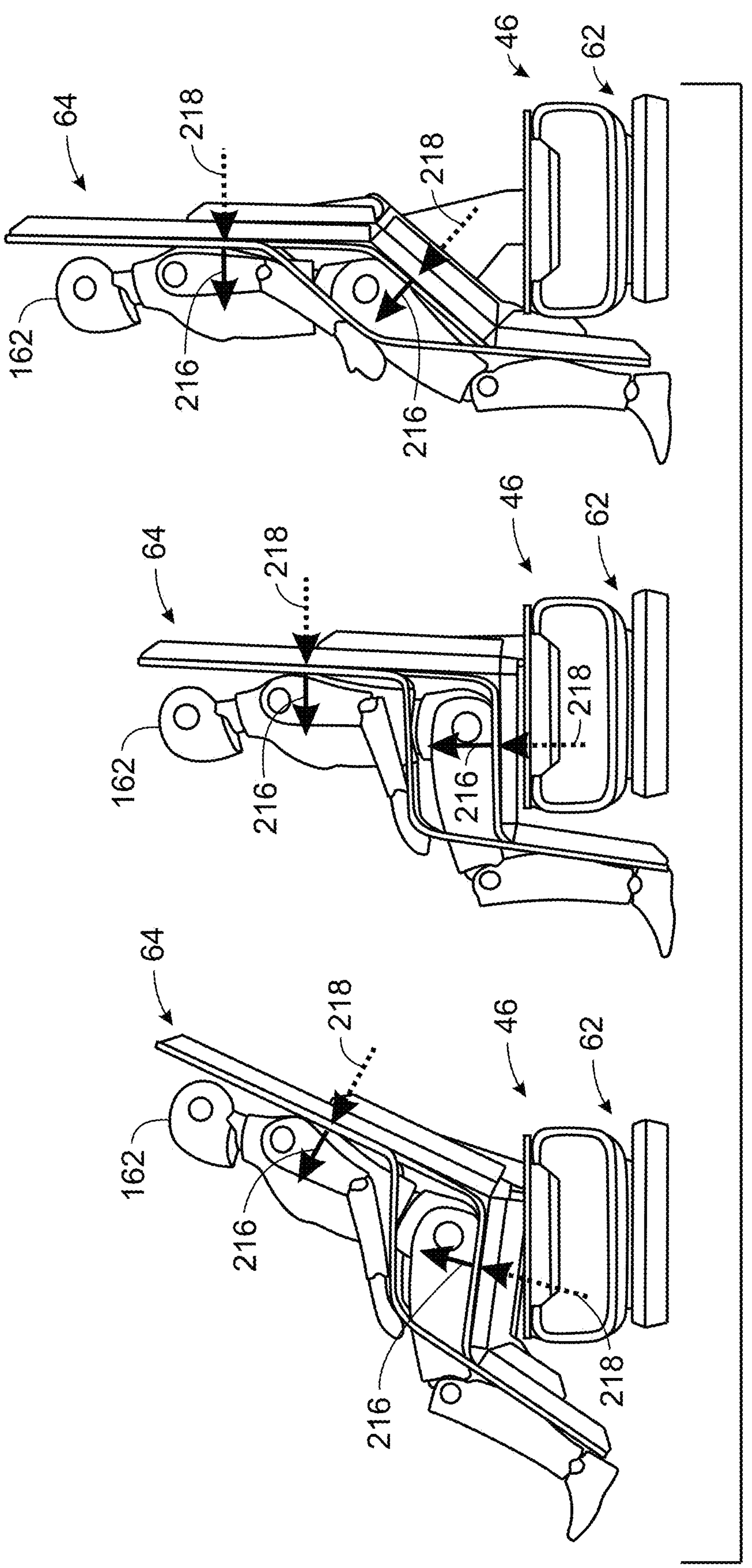
FIG. 13 is a schematic diagram illustrating adaptively assisted egress, in accordance with aspects of the present disclosure.

FIG. 13 is a schematic diagram illustrating adaptively assisted egress. On the left side of FIG. 13, the top patient support 64 is in the third configuration (i.e., zero-gravity configuration). In the middle of FIG. 13, the top patient support 64 is in the second configuration (i.e., upright-chair configuration). On the right side of FIG. 13, the top patient support 64 is in the fourth configuration (i.e., vertical configuration) to enable the patient 162 to egress. The top patient support 64 transitions from the third configuration to the second configuration, and then transitions to the fourth configuration for egress. Arrows 216 indicate the patient's own effort. Arrows 218 indicate the computed forces applied to adaptively assist the patient 162.

Figure 14:
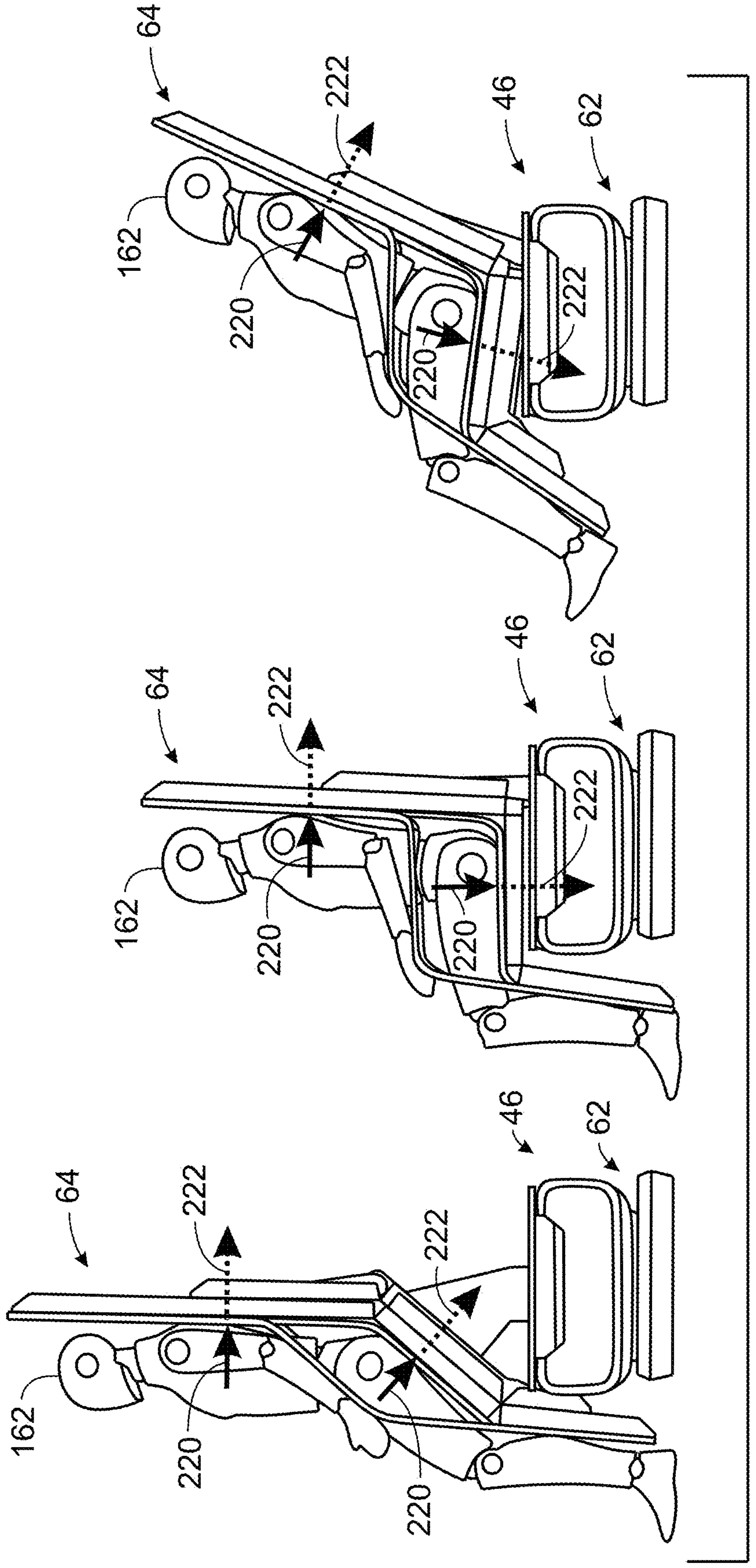
FIG. 14 is a schematic diagram illustrating adaptively assisted ingress, in accordance with aspects of the present disclosure.
Figure 15:
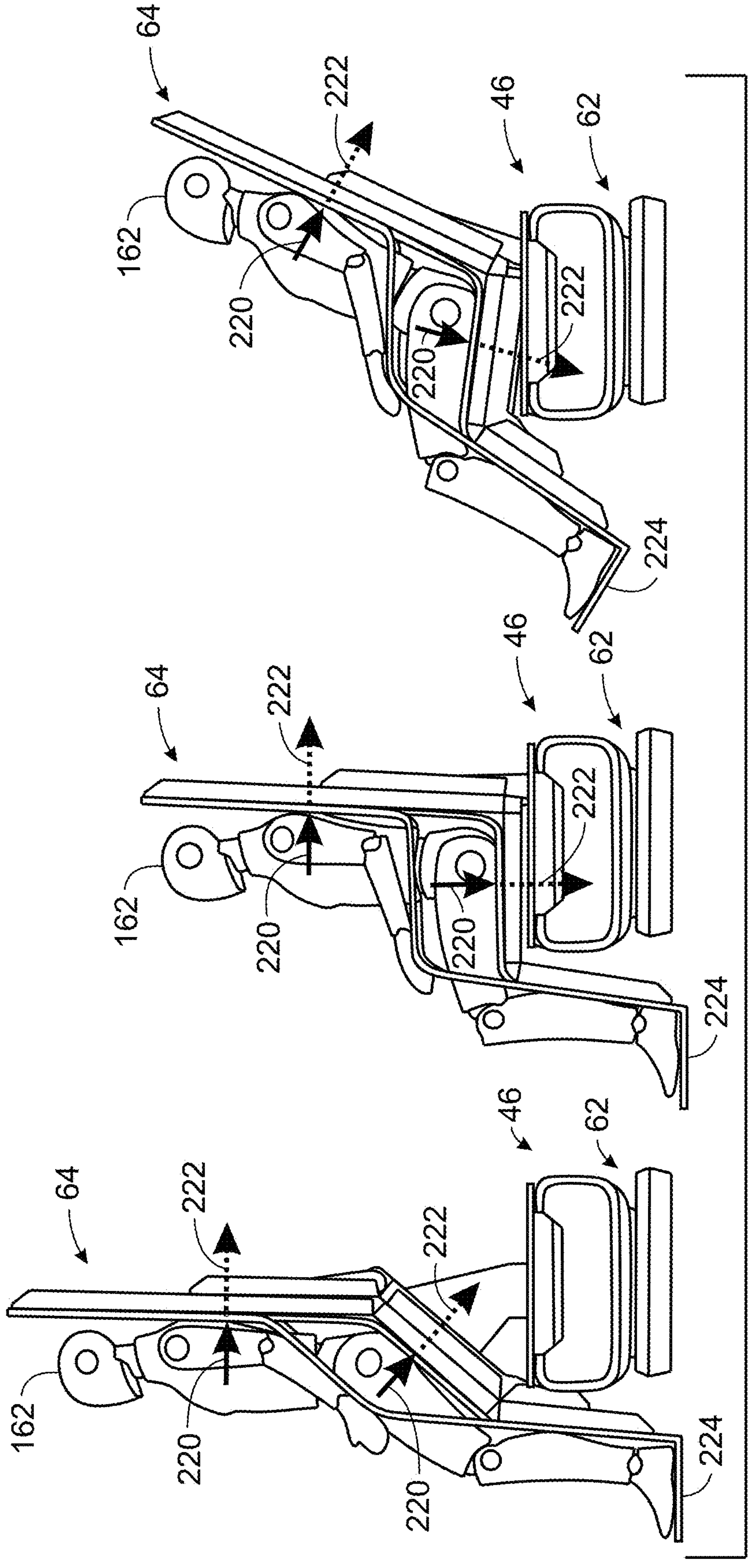
FIG. 15 is a schematic diagram illustrating adaptively assisted ingress, in accordance with aspects of the present disclosure.

FIG. 14 is a schematic diagram illustrating adaptively assisted ingress. On the left side of FIG. 14, the top patient support 64 is in the fourth configuration (i.e., vertical configuration) to enable the patient 162 to ingress. In the middle of FIG. 14, the top patient support 64 is in the second configuration (i.e., upright-chair configuration). On the right side of FIG. 13, the top patient support 64 is in the third configuration (i.e., zero-gravity configuration). The top patient support 64 transitions from the fourth configuration to the second configuration, and then transitions to the third configuration for ingress. Arrows 220 indicate the patient's own effort. Arrows 222 indicate the computed forces applied to adaptively assist the patient 162. In certain embodiments, the top patient support 64 includes a footrest support section 224 (e.g., coupled to the feed-end support section 70 in FIG. 2) that serves as a footrest that articulates through various configurations during the patient support articulation as depicted in FIG. 15. The footrest support section 224 is configured to provide additional support during ingress/egress. The footrest support section 224 is configured to become coplanar/horizonal was the rest of the top patient support 64 when in a horizontal configuration (as depicted in FIG. 7) during patient transfer into the gantry bore.

Technical effects of the disclosed embodiments include enabling overcoming physical challenges in patient handling and positioning during an imaging procedure while also enabling these tasks to be performed without necessitating additional staff. The articulating support is configured to assume various physically advantageous configurations to assist patient and staff through the patient loading, off-loading, and positioning maneuvers. Technical effects of the disclosed embodiments include providing the flexibility of loading and off-loading the patient with equal ease from either side of the patient table to accommodate for site conditions.

Technical effects of the disclosed embodiments include automatically adapting an articulating configuration to fulfill the assistive needs of various patients, rather than standardizing the articulated operation. Technical effects of the disclosed embodiments include enabling various articulating elements of the patient support to be selectively articulated (independent of other elements) for a certain extent of their travel while also enabling a concerted articulation of multiple elements in tandem, thereby progressively and effectively adapting to the patient's own effort to make the experience as natural as possible (while providing assistance during ingress or egress). Technical effects of the disclosed embodiments include eliminating any counter-assistive maneuvers of the articulating patient support that may be caused due to exceedingly high assistive force being generated or exerting less than effective assistive force depriving the patient of an assisted ingress or egress experience.

Technical effects of the disclosed embodiments include providing an improved experience for imaging technologists/support staff relative to the laborious and time-consuming process of patient handling and positioning during imaging procedures. Technical effects of the disclosed embodiments include increasing throughput and eliminating the need for extra staff to assist with patient handling and positioning tasks. Technical effects of the disclosed embodiments include providing an enhanced sense of empowerment, dignity, and safety for the patient.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The disclosure also provides support for a patient table for a medical imaging system, comprising: a multi-layered patient support comprising a top patient support configured to articulate and a bottom patient support, wherein the multi-layered patient support is configured to support a subject to be imaged, and wherein the top patient support is configured to move between a first configuration where the top patient support is flat and horizontal to support the subject in a recumbent position and a second configuration where the top patient support is in an upright-chair configuration to support the subject in an upright seated position; and a platform, wherein the platform is coupled to and supports the multi-layered patient support, and wherein the platform is configured to keep the multi-layered patient support at a desired elevation and to move the multi-layered patient support into and out of a bore of a gantry of the medical imaging system for an imaging procedure performed on the subject. In a first example of the patient table, the platform comprises a static base, and wherein the platform is configured to move the bottom patient support separately from the top patient support in a vertical direction relative to the static base via a first vertical lift. In a second example of the patient table, optionally including the first example, the platform is configured to move the top patient support from the bottom patient support in the vertical direction relative to the static base via a second vertical lift. In a third example of the patient table, optionally including one or both of the first and second examples, the second vertical lift is configured to be coupled to the top patient support in the second configuration and is configured to be decoupled from the top patient support in the first configuration. In a fourth example of the patient table, optionally including one or more of each of the first through third examples, the platform is configured to tilt the top patient support to move to a third configuration in a transition between the first configuration and the second configuration, wherein in the third configuration the top patient support is configured to support the subject in a zero-gravity position. In a fifth example of the patient table, optionally including one or more of each of the first through fourth examples, the platform is configured to bidirectionally tilt the top patient support between the second configuration and the third configuration. In a sixth example of the patient table, optionally including one or more of each of the first through fifth examples, the platform, when top patient support is in the third configuration, is configured to rotate the top patient support about a vertical axis during the transition between the first configuration and the second configuration. In a seventh example of the patient table, optionally including one or more of each of the first through sixth examples, the platform, when the top patient support is in the third configuration, is configured to rotate the top patient support between a first orientation where the subject faces away from the patient table and a second orientation where the subject faces toward a longitudinal end of the patient table. In an eighth example of the patient table, optionally including one or more of each of the first through seventh examples, the top patient support comprises a patient interfacing layer comprising a central portion and hand rests flanking the central portion, and wherein the hand rests move with the subject between the first configuration and the second configuration. In a ninth example of the patient table, optionally including one or more of each of the first through eighth examples, each of hand rests comprises respective hinge mechanisms that are configured to enable a respective hand rest to flex at two locations to move a portion of the respective hand rest away from the central portion when transitioning to the second configuration and to move the portion of the respective hand rest toward the central portion when transitioning to the first configuration. In a tenth example of the patient table, optionally including one or more of each of the first through ninth examples, the patient table further comprises: a first set of sensors coupled to the multi-layered patient support; a plurality of actuators coupled to multi-layered patient support; and a controller comprising a memory and a processing system comprising one or more processors, wherein the controller is configured to receive feedback from the first set of sensors, to estimate both a subject's pose and exerted physical effort towards either ingress into or egress from the top patient support based on the feedback, to calculate respective assistive forces needed at various portions of the top patient support based on the subject's pose and exerted physical effort, and to provide control signals to the plurality of actuators to deliver the respective assistive forces at the various portions of the top patient support. In an eleventh example of the patient table, optionally including one or more of each of the first through tenth examples, the patient table further comprises one or more additional sensors configured to monitor the subject supported on the multi-layered patient support, wherein the controller is configured to receive additional feedback from the one or more additional sensors and to provide control signals, based on the additional feedback, to the plurality of actuators to keep the subject from colliding with an object within a room that the medical imaging system is disposed within and/or to keep the subject from falling from the multi-layered patient support.

The disclosure also provides support for a medical imaging system, comprising: a gantry having a bore and coupled to imaging components configured to acquire imaging data of a subject; and a patient table integrated with the gantry, comprising: a multi-layered patient support comprising a top patient support configured to articulate and a bottom patient support, wherein the multi-layered patient support is configured to support the subject to be imaged, and wherein the top patient support is configured to move between a first configuration where the top patient support is flat and horizontal to support the subject in a recumbent position and a second configuration where the top patient support is in an upright-chair configuration to support the subject in an upright seated position; and a platform, wherein the platform is coupled to and supports the multi-layered patient support, and wherein the platform is configured to move the multi-layered patient support into and out of the bore of the gantry of the medical imaging system for an imaging procedure performed on the subject. In a first example of the medical imaging system, the platform comprises a static base, wherein the platform is configured to move the bottom patient support separately from the top patient support in a vertical direction relative to the static base via a first vertical lift, wherein the platform is configured to move the top patient support from the bottom patient support in the vertical direction relative to the static base via a second vertical lift, and wherein the second vertical lift is configured to be coupled to the top patient support in the second configuration and is configured to be decoupled from the top patient support in the first configuration. In a second example of the medical imaging system, optionally including the first example, the platform is configured to tilt the top patient support to move to a third configuration in a transition between the first configuration and the second configuration, wherein in the third configuration the top patient support is configured to support the subject in a zero-gravity position, and wherein the platform is configured to bidirectionally tilt the top patient support between the second configuration and the third configuration. In a third example of the medical imaging system, optionally including one or both of the first and second examples, the platform, when top patient support is in the third configuration, is configured to rotate the top patient support about a vertical axis during the transition between the first configuration and the second configuration. In a fourth example of the medical imaging system, optionally including one or more or each of the first through third examples, the platform, when the top patient support is in the third configuration, is configured to rotate the top patient support between a first orientation where the subject faces away from the patient table and a second orientation where the subject faces toward a longitudinal end of the patient table. In a fifth example of the medical imaging system, optionally including one or more or each of the first through fourth examples, the top patient support comprises a patient interfacing layer comprising a central portion and hand rests flanking the central portion, and wherein the hand rests move with the subject between the first configuration and the second configuration. In a sixth example of the medical imaging system, optionally including one or more or each of the first through fifth examples, each of hand rests comprises respective hinge mechanisms that are configured to enable a respective hand rest to flex at two locations to move a portion of the respective hand rest away from the central portion when transitioning to the second configuration and to move the portion of the respective hand rest toward the central portion when transitioning to the first configuration.

The disclosure also provides support for a medical imaging system, comprising: a gantry having a bore and coupled to imaging components configured to acquire imaging data of a subject; and a patient table integrated with the gantry comprising: a multi-layered patient support comprising a top patient support configured to articulate and a bottom patient support, wherein the multi-layered patient support is configured to support the subject to be imaged, and wherein the top patient support is configured to move between a first configuration where the top patient support is flat and horizontal to support the subject in a recumbent position and a second configuration where the top patient support is in an upright-chair configuration to support the subject in an upright seated position; a platform, wherein the platform is coupled to and supports the multi-layered patient support, and wherein the platform is configured to move the multi-layered patient support into and out of the bore of the gantry of the medical imaging system for an imaging procedure performed on the subject; a plurality of sensors coupled to the multi-layered patient support; a plurality of actuators coupled to multi-layered patient support; and a controller comprising a memory and a processing system comprising one or more processors, wherein the controller is configured to receive feedback from the plurality of sensors, to estimate both a subject's pose and exerted physical effort towards either ingress into or egress from the top patient support based on the feedback, to calculate respective assistive forces needed at various portions of the top patient support based on the subject's pose and exerted physical effort, and to provide control signals to the plurality of actuators to deliver the respective assistive forces at the various portions of the top patient support.

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A patient table for a medical imaging system, comprising:

a multi-layered patient support comprising a top patient support configured to articulate and a bottom patient support, wherein the multi-layered patient support is configured to support a subject to be imaged, wherein the top patient support is configured to automatically move between a first configuration where the top patient support is flat and horizontal to support the subject in a recumbent position and a second configuration where the top patient support is in an upright-chair configuration to support the subject in an upright seated position, and wherein the bottom patient support is configured to physically engage the top patient support in the first configuration, and the bottom patient support is configured to be physically disengaged from the top patient support in the second configuration; and a platform, wherein the platform is coupled to and supports both the top patient support and the bottom patient support of the multi-layered patient support, and wherein the platform is configured to keep the multi-layered patient support at a desired elevation and to move the multi-layered patient support into and out of a bore of a gantry of the medical imaging system for an imaging procedure performed on the subject.

2. The patient table of claim 1, wherein the platform comprises a static base, wherein the platform is configured to move the bottom patient support separately from the top patient support in a vertical direction relative to the static base via a first vertical lift.

3. The patient table of claim 2, and wherein the platform is configured to move the top patient support from the bottom patient support in the vertical direction relative to the static base via a second vertical lift.

4. The patient table of claim 3, wherein the second vertical lift is configured to be coupled to the top patient support in the second configuration and is configured to be decoupled from the top patient support in the first configuration.

5. The patient table of claim 1, wherein the platform is configured to tilt the top patient support to move to a third configuration in a transition between the first configuration and the second configuration, wherein in the third configuration the top patient support is configured to support the subject in a zero-gravity position.

6. The patient table of claim 5, wherein the platform is configured to bidirectionally tilt the top patient support between the second configuration and the third configuration.

7. The patient table of claim 5, wherein the platform, when top patient support is in the third configuration, is configured to rotate the top patient support about a vertical axis during the transition between the first configuration and the second configuration.

8. The patient table of claim 7, wherein the platform, when the top patient support is in the third configuration, is configured to rotate the top patient support between a first orientation where the subject faces away from the patient table and a second orientation where the subject faces toward a longitudinal end of the patient table.

9. The patient table of claim 1, wherein the top patient support comprises a patient interfacing layer comprising a central portion and hand rests flanking the central portion, and wherein the hand rests move with the subject between the first configuration and the second configuration.

10. The patient table of claim 9, wherein each of the hand rests comprises respective hinge mechanisms that are configured to enable a respective hand rest to flex at two locations to move a portion of the respective hand rest away from the central portion when transitioning to the second configuration and to move the portion of the respective hand rest toward the central portion when transitioning to the first configuration.

11. The patient table of claim 1, further comprising:

a first set of sensors coupled to the multi-layered patient support;

a plurality of actuators coupled to multi-layered patient support; and a controller comprising a memory and a processing system comprising one or more processors, wherein the controller is configured to receive feedback from the first set of sensors, to estimate both a subject's pose and exerted physical effort towards either ingress into or egress from the top patient support based on the feedback, to calculate respective assistive forces needed at various portions of the top patient support based on the subject's pose and exerted physical effort, and to provide control signals to the plurality of actuators to deliver the respective assistive forces at the various portions of the top patient support.

12. The patient table of claim 11, further comprising one or more additional sensors configured to monitor the subject supported on the multi-layered patient support, wherein the controller is configured to receive additional feedback from the one or more additional sensors and to provide control signals, based on the additional feedback, to the plurality of actuators either to keep the subject from colliding with an object within a room that the medical imaging system is disposed within or to keep the subject from falling from the multi-layered patient support.

13. A medical imaging system, comprising:

a gantry having a bore and coupled to imaging components configured to acquire imaging data of a subject; and a patient table integrated with the gantry, comprising:

a multi-layered patient support comprising a top patient support configured to articulate and a bottom patient support, wherein the multi-layered patient support is configured to support the subject to be imaged, wherein the top patient support is configured to automatically move between a first configuration where the top patient support is flat and horizontal to support the subject in a recumbent position and a second configuration where the top patient support is in an upright-chair configuration to support the subject in an upright seated position, and wherein the bottom patient support is configured to physically engage the top patient support in the first configuration, and the bottom patient support is configured to be physically disengaged from the top patient support in the second configuration; and a platform, wherein the platform is coupled to and supports both the top patient support and the bottom patient support of the multi-layered patient support, and wherein the platform is configured to move the multi-layered patient support into and out of the bore of the gantry of the medical imaging system for an imaging procedure performed on the subject.

14. The medical imaging system of claim 13, wherein the platform comprises a static base, wherein the platform is configured to move the bottom patient support separately from the top patient support in a vertical direction relative to the static base via a first vertical lift, wherein the platform is configured to move the top patient support from the bottom patient support in the vertical direction relative to the static base via a second vertical lift, and wherein the second vertical lift is configured to be coupled to the top patient support in the second configuration and is configured to be decoupled from the top patient support in the first configuration.

15. The medical imaging system of claim 13, wherein the platform is configured to tilt the top patient support to move to a third configuration in a transition between the first configuration and the second configuration, wherein in the third configuration the top patient support is configured to support the subject in a zero-gravity position, and wherein the platform is configured to bidirectionally tilt the top patient support between the second configuration and the third configuration.

16. The medical imaging system of claim 15, wherein the platform, when top patient support is in the third configuration, is configured to rotate the top patient support about a vertical axis during the transition between the first configuration and the second configuration.

17. The medical imaging system of claim 16, wherein the platform, when the top patient support is in the third configuration, is configured to rotate the top patient support between a first orientation where the subject faces away from the patient table and a second orientation where the subject faces toward a longitudinal end of the patient table.

18. The medical imaging system of claim 13, wherein the top patient support comprises a patient interfacing layer comprising a central portion and hand rests flanking the central portion, and wherein the hand rests move with the subject between the first configuration and the second configuration.

19. The medical imaging system of claim 18, wherein each of hand rests comprises respective hinge mechanisms that are configured to enable a respective hand rest to flex at two locations to move a portion of the respective hand rest away from the central portion when transitioning to the second configuration and to move the portion of the respective hand rest toward the central portion when transitioning to the first configuration.

20. A medical imaging system, comprising:

a gantry having a bore and coupled to imaging components configured to acquire imaging data of a subject; and a patient table integrated with the gantry comprising:

a multi-layered patient support comprising a top patient support configured to articulate and a bottom patient support, wherein the multi-layered patient support is configured to support the subject to be imaged, wherein the top patient support is configured to automatically move between a first configuration where the top patient support is flat and horizontal to support the subject in a recumbent position and a second configuration where the top patient support is in an upright-chair configuration to support the subject in an upright seated position, and wherein the bottom patient support is configured to physically engage the top patient support in the first configuration, and the bottom patient support is configured to be physically disengaged from the top patient support in the second configuration;

a platform, wherein the platform is coupled to and supports both the top patient support and the bottom patient support of the multi-layered patient support, and wherein the platform is configured to move the multi-layered patient support into and out of the bore of the gantry of the medical imaging system for an imaging procedure performed on the subject;

a plurality of sensors coupled to the multi-layered patient support;

a plurality of actuators coupled to multi-layered patient support; and a controller comprising a memory and a processing system comprising one or more processors, wherein the controller is configured to receive feedback from the plurality of sensors, to estimate both a subject's pose and exerted physical effort towards either ingress into or egress from the top patient support based on the feedback, to calculate respective assistive forces needed at various portions of the top patient support based on the subject's pose and exerted physical effort, and to provide control signals to the plurality of actuators to deliver the respective assistive forces at the various portions of the top patient support.

* * * * *